＝

US011946084B2

(12) United States Patent
Guo et al.

(10) Patent No.: US 11,946,084 B2
(45) Date of Patent: Apr. 2, 2024

(54) FUSION PROTEIN COMPRISING A PAB1 ELEMENT AND AN EIF4G ELEMENT AND USE OF THE FUSION PROTEIN FOR IMPROVING PROTEIN SYNTHESIS

(71) Applicant: KangMa-Healthcode (Shanghai) Biotech Co., Ltd, Shanghai (CN)

(72) Inventors: Min Guo, Shanghai (CN); Shuailong Liu, Shanghai (CN); Xue Yu, Shanghai (CN)

(73) Assignee: KANGMA-HEALTHCODE (SHANGHAI) BIOTECH CO., LTD, Shanghai (CN)

( * ) Notice: Subject to any disclaimer, the term of this patent is extended or adjusted under 35 U.S.C. 154(b) by 496 days.

(21) Appl. No.: 16/633,524

(22) PCT Filed: Dec. 13, 2017

(86) PCT No.: PCT/CN2017/115972
§ 371 (c)(1),
(2) Date: May 22, 2020

(87) PCT Pub. No.: WO2019/024379
PCT Pub. Date: Feb. 7, 2019

(65) Prior Publication Data
US 2021/0189449 A1 Jun. 24, 2021

(30) Foreign Application Priority Data
Jul. 31, 2017 (CN) .......................... 201710642517.4

(51) Int. Cl.
*C12P 21/00* (2006.01)
*C07K 7/06* (2006.01)
*C12N 15/86* (2006.01)

(52) U.S. Cl.
CPC ................ *C12P 21/00* (2013.01); *C07K 7/06* (2013.01); *C12N 15/86* (2013.01); *C07K 2319/02* (2013.01)

(58) Field of Classification Search
CPC ........... C12P 21/00; C12P 21/02; C07K 7/06; C07K 2319/02; C07K 14/39; C07K 2319/00; C12N 15/86; C12N 15/62; C12N 9/0069; C12N 9/14; C12Y 113/12007; C12Y 306/04013
See application file for complete search history.

(56) References Cited

U.S. PATENT DOCUMENTS
2012/0090052 A1 4/2012 Molinero et al.

FOREIGN PATENT DOCUMENTS
| CN | 103060334 A | 4/2013 |
|---|---|---|
| CN | 106978349 A | 7/2017 |
| WO | 9960408 A2 | 11/1999 |
| WO | 0053779 A1 | 9/2000 |
| WO | 2014144583 A2 | 9/2014 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Brambilla et al., Yeast 36:23-34, 2019.*
Jia et al., GenBank accession No. XP_056037140, May 19, 2023.*
Tarun et al., PNAS 94:9046-9051, 1997.*
Marcotte et al., Science 285:751-753, 1999.*
International Search Report for corresponding PCT Application No. PCT/CN2017/115972 dated May 3, 2018.
Archer, S.K. et al., "Probing the Closed-Loop Model of mRNA Translation in Living Cells", RNA Biology, 12(3), Mar. 31, 2015 (Mar. 31, 2015), ISSN: 1547-6286, abstract.
Lall, S. et al., "Caenorhabditis Elegans Decapping Proteins: Localization and Functional Analysis of Dcp1, Dcp2, and DcpS during Embryogenesis", Molecular Biology of the Cell, 16(12), Dec. 31, 2005 (Dec. 31, 2005), ISSN: 1939-4586, abstract.
European Search Report for corresponding EP Application No. 7920595.0-1111 dated Mar. 16, 2021.
Wang et al., "Stoichiometry and Change of the mRNA Closed-Loop Factors as Translating Ribosomes Transit from Initiation to Elongation", PLOS One IDOI:10.1371/journal.pone.0150616 Mar. 8, 2016, XP55781999A.
Chritton et al., "A Role for the Poly(A)-binding Protein Pab1pin PUF Protein-mediated Repression*", Journal of Biological Chemistry, vol. 286 • No. 38 • Sep. 23, 2011, XP55782014A.

* cited by examiner

*Primary Examiner* — Delia M Ramirez
(74) *Attorney, Agent, or Firm* — Wood, Phillips, Katz, Clark & Mortimer

(57) ABSTRACT

Provided are a fusion protein comprising a Pab1 element and an eIF4G element and a preparation method therefor. The fusion protein can improve in-vitro translation efficiency. A constitutive or inducible promoter (for example, pK1PGK1) may also be inserted in front of eIF4G in the fusion protein for increasing in-vitro protein synthesis ability.

14 Claims, 7 Drawing Sheets
Specification includes a Sequence Listing.

SEQUENCE LISTING

<160> NUMBER OF SEQ ID NOS: 66

<210> SEQ ID NO 1
<211> LENGTH: 592
<212> TYPE: PRT
<213> ORGANISM: Kluyveromyces lactis

<400> SEQUENCE: 1

```
Met Ser Asp Ile Thr Glu Lys Thr Ala Glu Gln Leu Glu Asn Leu Gln
1               5                   10                  15

Ile Asn Asp Asp Gln Gln Pro Ala Gln Ser Ala Ser Ala Pro Ser Thr
            20                  25                  30

Ser Ala Ser Glu Ser Glu Ala Ser Ser Val Ser Lys Val Glu Asn Asn
        35                  40                  45

Asn Ala Ser Leu Tyr Val Gly Glu Leu Asp Pro Asn Ile Thr Glu Ala
    50                  55                  60

Leu Leu Tyr Asp Val Phe Ser Pro Leu Gly Pro Ile Ser Ser Ile Arg
65                  70                  75                  80

Val Cys Arg Asp Ala Val Thr Lys Ala Ser Leu Gly Tyr Ala Tyr Val
                85                  90                  95

Asn Tyr Thr Asp Tyr Glu Ala Gly Lys Lys Ala Ile Gln Glu Leu Asn
            100                 105                 110

Tyr Ala Glu Ile Asn Gly Arg Pro Cys Arg Ile Met Trp Ser Glu Arg
        115                 120                 125

Asp Pro Ala Ile Arg Lys Lys Gly Ser Gly Asn Ile Phe Ile Lys Asn
    130                 135                 140

Leu His Pro Ala Ile Asp Asn Lys Ala Leu His Glu Thr Phe Ser Thr
145                 150                 155                 160

Phe Gly Glu Val Leu Ser Cys Lys Val Ala Leu Asp Glu Asn Gly Asn
                165                 170                 175

Ser Arg Gly Phe Gly Phe Val His Phe Lys Glu Glu Ser Asp Ala Lys
            180                 185                 190

Asp Ala Ile Glu Ala Val Asn Gly Met Leu Met Asn Gly Leu Glu Val
        195                 200                 205

Tyr Val Ala Met His Val Pro Lys Lys Asp Arg Ile Ser Lys Leu Glu
    210                 215                 220

Glu Ala Lys Ala Asn Phe Thr Asn Ile Tyr Val Lys Asn Ile Asp Val
225                 230                 235                 240

Glu Thr Thr Asp Glu Glu Phe Glu Gln Leu Phe Ser Gln Tyr Gly Glu
                245                 250                 255

Ile Val Ser Ala Ala Leu Glu Lys Asp Ala Glu Gly Lys Pro Lys Gly
            260                 265                 270

Phe Gly Phe Val Asn Phe Val Asp His Asn Ala Ala Ala Lys Ala Val
        275                 280                 285

Glu Glu Leu Asn Gly Lys Glu Phe Lys Ser Gln Ala Leu Tyr Val Gly
    290                 295                 300

Arg Ala Gln Lys Lys Tyr Glu Arg Ala Glu Leu Lys Lys Gln Tyr
305                 310                 315                 320
```

```
Glu Gln Tyr Arg Leu Glu Lys Leu Ala Lys Phe Gln Gly Val Asn Leu
            325                 330                 335

Phe Ile Lys Asn Leu Asp Asp Ser Ile Asp Asp Glu Lys Leu Lys Glu
            340                 345                 350

Glu Phe Ala Pro Tyr Gly Thr Ile Thr Ser Ala Arg Val Met Arg Asp
            355                 360                 365

Gln Glu Gly Asn Ser Lys Gly Phe Gly Phe Val Cys Phe Ser Ser Pro
        370                 375                 380

Glu Glu Ala Thr Lys Ala Met Thr Glu Lys Asn Gln Gln Ile Val Ala
385                 390                 395                 400

Gly Lys Pro Leu Tyr Val Ala Ile Ala Gln Arg Lys Asp Val Arg Arg
            405                 410                 415

Ser Gln Leu Ala Gln Gln Ile Gln Ala Arg Asn Gln Ile Arg Phe Gln
            420                 425                 430

Gln Gln Gln Gln Gln Ala Ala Ala Ala Ala Gly Met Pro Gly
        435                 440                 445

Gln Tyr Met Pro Gln Met Phe Tyr Gly Val Met Ala Pro Arg Gly Phe
    450                 455                 460

Pro Gly Pro Asn Pro Gly Met Asn Gly Pro Met Gly Ala Gly Ile Pro
465                 470                 475                 480

Lys Asn Gly Met Val Pro Pro Gln Gln Phe Ala Gly Arg Pro Asn
                485                 490                 495

Gly Pro Met Tyr Gln Gly Met Pro Pro Gln Asn Gln Phe Pro Arg His
                500                 505                 510

Gln Gln Gln His Tyr Ile Gln Gln Lys Gln Arg Gln Ala Leu Gly
            515                 520                 525

Glu Gln Leu Tyr Lys Lys Val Ser Ala Lys Ile Asp Asp Glu Asn Ala
    530                 535                 540

Ala Gly Lys Ile Thr Gly Met Ile Leu Asp Leu Pro Pro Gln Gln Val
545                 550                 555                 560

Ile Gln Leu Leu Asp Asn Asp Glu Gln Phe Gln Gln Phe Gln Glu
                565                 570                 575

Ala Leu Ala Ala Tyr Glu Asn Phe Lys Lys Glu Gln Glu Ala Gln Ala
    580                 585                 590

<210> SEQ ID NO 2
<211> LENGTH: 1021
<212> TYPE: PRT
<213> ORGANISM: Kluyveromyces lactis

<400> SEQUENCE: 2

Met Gly Glu Pro Thr Ser Asp Gln Gln Pro Ala Val Glu Ala Pro Val
1               5                   10                  15

Val Gln Glu Glu Thr Thr Ser Ser Pro Gln Lys Asn Ser Gly Tyr Val
            20                  25                  30

Lys Asn Thr Ala Gly Ser Gly Ala Pro Arg Asn Gly Lys Tyr Asp Gly
        35                  40                  45

Asn Arg Lys Asn Ser Arg Pro Tyr Asn Gln Arg Gly Asn Asn Asn Asn
    50                  55                  60

Asn Asn Gly Ser Ser Ser Asn Lys His Tyr Gln Lys Tyr Asn Gln Pro
65                  70                  75                  80

Ala Tyr Gly Val Ser Ala Gly Tyr Ile Pro Asn Tyr Gly Val Ser Ala
                85                  90                  95

Glu Tyr Asn Pro Leu Tyr Tyr Asn Gln Tyr Gln Gln Gln Gln Leu
            100                 105                 110
```

```
Tyr Ala Ala Ala Tyr Gln Thr Pro Met Ser Gly Gln Gly Tyr Val Pro
            115                 120                 125

Pro Val Val Ser Pro Ala Ala Val Ser Ala Lys Pro Ala Lys Val Glu
        130                 135                 140

Ile Thr Asn Lys Ser Gly Glu His Ile Asp Ile Ala Ser Ile Ala His
145                 150                 155                 160

Pro His Thr His Ser His Ser Gln Ser His Ser Arg Ala Val Pro Val
                165                 170                 175

Val Ser Pro Pro Ala Asn Val Thr Val Ala Ala Ala Val Ser Ser Ser
        180                 185                 190

Val Ser Pro Ser Ala Ser Pro Ala Val Lys Val Gln Ser Pro Ala Ala
        195                 200                 205

Asn Gly Lys Glu Gln Ser Pro Ala Lys Pro Glu Glu Pro Lys Lys Asp
        210                 215                 220

Thr Leu Ile Val Asn Asp Phe Leu Glu Gln Val Lys Arg Arg Lys Ala
225                 230                 235                 240

Ala Leu Ala Ala Lys Lys Ala Val Glu Glu Lys Gly Pro Glu Glu Pro
                245                 250                 255

Lys Glu Ser Val Val Gly Thr Asp Thr Asp Ala Ser Val Asp Thr Lys
                260                 265                 270

Thr Gly Pro Thr Ala Thr Glu Ser Ala Lys Ser Glu Glu Ala Gln Ser
            275                 280                 285

Glu Ser Gln Glu Lys Thr Lys Glu Glu Ala Pro Ala Glu Pro Lys Pro
        290                 295                 300

Leu Thr Leu Ala Glu Lys Leu Arg Leu Lys Arg Met Glu Ala Ala Lys
305                 310                 315                 320

Gln Ala Ser Ala Lys Thr Glu Glu Leu Lys Thr Glu Glu Ser Lys Pro
                325                 330                 335

Glu Glu Thr Lys Thr Glu Glu Leu Lys Thr Glu Glu Ser Lys Pro Glu
            340                 345                 350

Glu Thr Lys Thr Glu Glu Leu Lys Thr Glu Glu Thr Lys Ser Glu Glu
            355                 360                 365

Leu Lys Thr Glu Glu Pro Lys Ala Glu Glu Ser Lys Ala Glu Glu Pro
        370                 375                 380

Lys Pro Glu Glu Pro Lys Thr Glu Glu Pro Thr Thr Glu Gln Pro Lys
385                 390                 395                 400

Ser Asp Glu Pro Lys Ser Glu Glu Ser Lys Thr Glu Glu Pro Lys Thr
                405                 410                 415

Glu Val Leu Lys Thr Glu Glu Pro Lys Ser Glu Glu Ser Lys Pro Ala
            420                 425                 430

Glu Pro Lys Thr Glu Glu Thr Ala Thr Glu Glu Thr Ala Thr Glu Ala
            435                 440                 445

Asn Ala Glu Glu Gly Glu Pro Ala Pro Ala Gly Pro Val Glu Thr Pro
        450                 455                 460

Ala Asp Val Glu Thr Lys Pro Arg Glu Glu Ala Glu Val Glu Asp Asp
465                 470                 475                 480

Gly Lys Ile Thr Met Thr Asp Phe Leu Gln Lys Leu Lys Glu Val Ser
                485                 490                 495

Pro Val Asp Asp Ile Tyr Ser Phe Gln Tyr Pro Ser Asp Ile Thr Pro
                500                 505                 510

Pro Asn Asp Arg Tyr Lys Lys Thr Ser Ile Lys Tyr Ala Tyr Gly Pro
            515                 520                 525
```

```
Asp Phe Leu Tyr Gln Phe Lys Glu Lys Val Asp Val Lys Tyr Asp Pro
            530                 535                 540

Ala Trp Met Ala Glu Met Thr Ser Lys Ile Val Ile Pro Pro Lys Lys
545                 550                 555                 560

Pro Gly Ser Ser Gly Arg Gly Glu Asp Arg Phe Ser Lys Gly Lys Val
                565                 570                 575

Gly Ser Leu Arg Ser Glu Gly Arg Ser Gly Ser Arg Ser Asn Ser Lys
            580                 585                 590

Lys Lys Ser Lys Arg Asp Asp Arg Lys Ser Asn Arg Ser Tyr Thr Ser
                595                 600                 605

Arg Lys Asp Arg Glu Arg Phe Arg Glu Glu Val Glu Glu Pro Lys
            610                 615                 620

Val Glu Val Ala Pro Leu Val Pro Ser Ala Asn Arg Trp Val Pro Lys
625                 630                 635                 640

Ser Lys Met Lys Lys Thr Glu Val Lys Leu Ala Pro Asp Gly Thr Glu
                645                 650                 655

Leu Tyr Asp Ala Glu Glu Ala Ser Arg Lys Met Lys Ser Leu Leu Asn
            660                 665                 670

Lys Leu Thr Leu Glu Met Phe Glu Pro Ile Ser Asp Asp Ile Met Lys
                675                 680                 685

Ile Ala Asn Gln Ser Arg Trp Glu Glu Lys Gly Glu Thr Leu Lys Ile
            690                 695                 700

Val Ile Gln Gln Ile Phe Asn Lys Ala Cys Asp Glu Pro His Trp Ser
705                 710                 715                 720

Ser Met Tyr Ala Gln Leu Cys Gly Lys Val Val Lys Asp Leu Asp Asp
                725                 730                 735

Ser Ile Lys Asp Ser Glu Thr Pro Asp Lys Thr Gly Ser His Leu Val
            740                 745                 750

Leu His Tyr Leu Val Gln Arg Cys Gln Thr Glu Phe Gln Thr Gly Trp
            755                 760                 765

Thr Asp Gln Leu Pro Thr Asn Glu Asp Gly Thr Pro Leu Gln Pro Glu
770                 775                 780

Met Met Ser Asp Glu Tyr Tyr Lys Met Ala Ala Ala Lys Arg Arg Gly
785                 790                 795                 800

Leu Gly Leu Val Arg Phe Ile Gly Phe Leu Tyr Arg Ser Asn Leu Leu
                805                 810                 815

Thr Ser Arg Met Val Phe Phe Cys Phe Lys Arg Leu Met Lys Asp Ile
            820                 825                 830

Gln Asn Ser Pro Thr Glu Asp Thr Leu Glu Ser Val Cys Glu Leu Leu
            835                 840                 845

Glu Thr Ile Gly Glu Gln Phe Glu Gly Ala Arg Ile Gln Val Thr Ala
850                 855                 860

Glu Ala Val Ile Glu Gly Ser Ser Leu Leu Asp Thr Leu Phe Asp Gln
865                 870                 875                 880

Ile Lys Asn Val Ile Glu Asn Gly Asp Ile Ser Ser Arg Ile Lys Phe
                885                 890                 895

Lys Leu Ile Asp Ile Val Glu Leu Arg Glu Lys Arg Asn Trp Asn Ser
            900                 905                 910

Lys Asn Lys Asn Asp Gly Pro Lys Thr Ile Ala Gln Ile His Glu Glu
                915                 920                 925

Glu Ala Leu Lys Arg Ala Leu Glu Glu Arg Glu Arg Glu Arg Asp Arg
930                 935                 940

His Gly Ser Arg Gly Gly Ser Arg Arg Met Asn Ser Glu Arg Asn Ser
```

-continued

```
                945                 950                 955                 960
Ser Arg Arg Asp Phe Ser Ser His Ser His Ser His Asn Gln Asn Arg
                    965                 970                 975

Asp Gly Phe Thr Thr Thr Arg Ser Ser Val Arg Tyr Ser Glu Pro
                980                 985                 990

Lys Lys Glu Glu Gln Ala Pro Thr Pro Thr Lys Ser Ser Gly Gly Ala
                995                1000                1005

Ala Asn Met Phe Asp Ala Leu Met Asp Ala Glu Asp Asp
                1010                1015                1020

<210> SEQ ID NO 3
<211> LENGTH: 1642
<212> TYPE: PRT
<213> ORGANISM: Artificial sequence
<220> FEATURE:
<223> OTHER INFORMATION: amino acid sequence of the fusion protein

<400> SEQUENCE: 3

Met Ser Asp Ile Thr Glu Lys Thr Ala Glu Gln Leu Glu Asn Leu Gln
1               5                   10                  15

Ile Asn Asp Asp Gln Gln Pro Ala Gln Ser Ala Ser Ala Pro Ser Thr
                20                  25                  30

Ser Ala Ser Glu Ser Glu Ala Ser Ser Val Ser Lys Val Glu Asn Asn
            35                  40                  45

Asn Ala Ser Leu Tyr Val Gly Glu Leu Asp Pro Asn Ile Thr Glu Ala
        50                  55                  60

Leu Leu Tyr Asp Val Phe Ser Pro Leu Gly Pro Ile Ser Ser Ile Arg
65              70                  75                  80

Val Cys Arg Asp Ala Val Thr Lys Ala Ser Leu Gly Tyr Ala Tyr Val
                85                  90                  95

Asn Tyr Thr Asp Tyr Glu Ala Gly Lys Lys Ala Ile Gln Glu Leu Asn
                100                 105                 110

Tyr Ala Glu Ile Asn Gly Arg Pro Cys Arg Ile Met Trp Ser Glu Arg
            115                 120                 125

Asp Pro Ala Ile Arg Lys Lys Gly Ser Gly Asn Ile Phe Ile Lys Asn
        130                 135                 140

Leu His Pro Ala Ile Asp Asn Lys Ala Leu His Glu Thr Phe Ser Thr
145             150                 155                 160

Phe Gly Glu Val Leu Ser Cys Lys Val Ala Leu Asp Glu Asn Gly Asn
                165                 170                 175

Ser Arg Gly Phe Gly Phe Val His Phe Lys Glu Glu Ser Asp Ala Lys
                180                 185                 190

Asp Ala Ile Glu Ala Val Asn Gly Met Leu Met Asn Gly Leu Glu Val
            195                 200                 205

Tyr Val Ala Met His Val Pro Lys Lys Asp Arg Ile Ser Lys Leu Glu
        210                 215                 220

Glu Ala Lys Ala Asn Phe Thr Asn Ile Tyr Val Lys Asn Ile Asp Val
225             230                 235                 240

Glu Thr Thr Asp Glu Glu Phe Glu Gln Leu Phe Ser Gln Tyr Gly Glu
                245                 250                 255

Ile Val Ser Ala Ala Leu Glu Lys Asp Ala Glu Gly Lys Pro Lys Gly
                260                 265                 270

Phe Gly Phe Val Asn Phe Val Asp His Asn Ala Ala Ala Lys Ala Val
            275                 280                 285

Glu Glu Leu Asn Gly Lys Glu Phe Lys Ser Gln Ala Leu Tyr Val Gly
```

```
                290                 295                 300
Arg Ala Gln Lys Lys Tyr Glu Arg Ala Glu Glu Leu Lys Lys Gln Tyr
305                 310                 315                 320

Glu Gln Tyr Arg Leu Glu Lys Leu Ala Lys Phe Gln Gly Val Asn Leu
                325                 330                 335

Phe Ile Lys Asn Leu Asp Asp Ser Ile Asp Asp Glu Lys Leu Lys Glu
                340                 345                 350

Glu Phe Ala Pro Tyr Gly Thr Ile Thr Ser Ala Arg Val Met Arg Asp
                355                 360                 365

Gln Glu Gly Asn Ser Lys Gly Phe Gly Phe Val Cys Phe Ser Ser Pro
                370                 375                 380

Glu Glu Ala Thr Lys Ala Met Thr Glu Lys Asn Gln Gln Ile Val Ala
385                 390                 395                 400

Gly Lys Pro Leu Tyr Val Ala Ile Ala Gln Arg Lys Asp Val Arg Arg
                405                 410                 415

Ser Gln Leu Ala Gln Gln Ile Gln Ala Arg Asn Gln Ile Arg Phe Gln
                420                 425                 430

Gln Gln Gln Gln Gln Ala Ala Ala Ala Ala Gly Met Pro Gly
                435                 440                 445

Gln Tyr Met Pro Gln Met Phe Tyr Gly Val Met Ala Pro Arg Gly Phe
450                 455                 460

Pro Gly Pro Asn Pro Gly Met Asn Gly Pro Met Gly Ala Gly Ile Pro
465                 470                 475                 480

Lys Asn Gly Met Val Pro Pro Gln Gln Phe Ala Gly Arg Pro Asn
                485                 490                 495

Gly Pro Met Tyr Gln Gly Met Pro Pro Gln Asn Gln Phe Pro Arg His
                500                 505                 510

Gln Gln His Tyr Ile Gln Gln Lys Gln Arg Gln Ala Leu Gly
                515                 520                 525

Glu Gln Leu Tyr Lys Lys Val Ser Ala Lys Ile Asp Asp Glu Asn Ala
                530                 535                 540

Ala Gly Lys Ile Thr Gly Met Ile Leu Asp Leu Pro Pro Gln Gln Val
545                 550                 555                 560

Ile Gln Leu Leu Asp Asn Asp Glu Gln Phe Glu Gln Phe Gln Glu
                565                 570                 575

Ala Leu Ala Ala Tyr Glu Asn Phe Lys Lys Glu Gln Glu Ala Gln Ala
                580                 585                 590

Gly Gly Gly Gly Ser Gly Gly Gly Ser Thr Gln Asp Glu Val Gln
                595                 600                 605

Gly Pro His Ala Gly Lys Ser Thr Val Gly Gly Gly Ser Gly Glu
                610                 615                 620

Pro Thr Ser Asp Gln Gln Pro Ala Val Glu Ala Pro Val Val Gln Glu
625                 630                 635                 640

Glu Thr Thr Ser Ser Pro Gln Lys Asn Ser Gly Tyr Val Lys Asn Thr
                645                 650                 655

Ala Gly Ser Gly Ala Pro Arg Asn Gly Lys Tyr Asp Gly Asn Arg Lys
                660                 665                 670

Asn Ser Arg Pro Tyr Asn Gln Arg Gly Asn Asn Asn Asn Asn Gly
                675                 680                 685

Ser Ser Ser Asn Lys His Tyr Gln Lys Tyr Asn Gln Pro Ala Tyr Gly
                690                 695                 700

Val Ser Ala Gly Tyr Ile Pro Asn Tyr Gly Val Ser Ala Glu Tyr Asn
705                 710                 715                 720
```

-continued

```
Pro Leu Tyr Tyr Asn Gln Tyr Gln Gln Gln Gln Leu Tyr Ala Ala
            725                 730                 735
Ala Tyr Gln Thr Pro Met Ser Gly Gln Gly Tyr Val Pro Val Val
            740                 745                 750
Ser Pro Ala Ala Val Ser Ala Lys Pro Ala Lys Val Glu Ile Thr Asn
            755                 760                 765
Lys Ser Gly Glu His Ile Asp Ile Ala Ser Ile Ala His Pro His Thr
770                 775                 780
His Ser His Ser Gln Ser His Ser Arg Ala Val Pro Val Val Ser Pro
785                 790                 795                 800
Pro Ala Asn Val Thr Val Ala Ala Val Ser Ser Ser Val Ser Pro
            805                 810                 815
Ser Ala Ser Pro Ala Val Lys Val Gln Ser Pro Ala Ala Asn Gly Lys
            820                 825                 830
Glu Gln Ser Pro Ala Lys Pro Glu Glu Pro Lys Lys Asp Thr Leu Ile
            835                 840                 845
Val Asn Asp Phe Leu Glu Gln Val Lys Arg Arg Lys Ala Ala Leu Ala
850                 855                 860
Ala Lys Lys Ala Val Glu Glu Lys Gly Pro Glu Glu Pro Lys Glu Ser
865                 870                 875                 880
Val Val Gly Thr Asp Thr Asp Ala Ser Val Asp Thr Lys Thr Gly Pro
            885                 890                 895
Thr Ala Thr Glu Ser Ala Lys Ser Glu Glu Ala Gln Ser Glu Ser Gln
            900                 905                 910
Glu Lys Thr Lys Glu Glu Ala Pro Ala Glu Pro Lys Pro Leu Thr Leu
            915                 920                 925
Ala Glu Lys Leu Arg Leu Lys Arg Met Glu Ala Ala Lys Gln Ala Ser
930                 935                 940
Ala Lys Thr Glu Glu Leu Lys Thr Glu Glu Ser Lys Pro Glu Glu Thr
945                 950                 955                 960
Lys Thr Glu Glu Leu Lys Thr Glu Glu Ser Lys Pro Glu Glu Thr Lys
            965                 970                 975
Thr Glu Glu Leu Lys Thr Glu Thr Lys Ser Glu Glu Leu Lys Thr
            980                 985                 990
Glu Glu Pro Lys Ala Glu Glu Ser  Lys Ala Glu Glu Pro  Lys Pro Glu
            995                 1000                1005
Glu Pro  Lys Thr Glu Glu Pro  Thr Thr Glu Gln Pro  Lys Ser Asp
     1010                 1015                 1020
Glu Pro  Lys Ser Glu Glu Ser  Lys Thr Glu Glu Pro  Lys Thr Glu
     1025                 1030                 1035
Val Leu  Lys Thr Glu Glu Pro  Lys Ser Glu Glu Ser  Lys Pro Ala
     1040                 1045                 1050
Glu Pro  Lys Thr Glu Glu Thr  Ala Thr Glu Glu Thr  Ala Thr Glu
     1055                 1060                 1065
Ala Asn  Ala Glu Glu Gly Glu  Pro Ala Pro Ala Gly  Pro Val Glu
     1070                 1075                 1080
Thr Pro  Ala Asp Val Glu Thr  Lys Pro Arg Glu Glu  Ala Glu Val
     1085                 1090                 1095
Glu Asp  Asp Gly Lys Ile Thr  Met Thr Asp Phe Leu  Gln Lys Leu
     1100                 1105                 1110
Lys Glu  Val Ser Pro Val Asp  Asp Ile Tyr Ser Phe  Gln Tyr Pro
     1115                 1120                 1125
```

```
Ser Asp Ile Thr Pro Pro Asn Asp Arg Tyr Lys Lys Thr Ser Ile
1130                1135                1140

Lys Tyr Ala Tyr Gly Pro Asp Phe Leu Tyr Gln Phe Lys Glu Lys
1145                1150                1155

Val Asp Val Lys Tyr Asp Pro Ala Trp Met Ala Glu Met Thr Ser
1160                1165                1170

Lys Ile Val Ile Pro Pro Lys Lys Pro Gly Ser Ser Gly Arg Gly
1175                1180                1185

Glu Asp Arg Phe Ser Lys Gly Lys Val Gly Ser Leu Arg Ser Glu
1190                1195                1200

Gly Arg Ser Gly Ser Arg Ser Asn Ser Lys Lys Ser Lys Arg
1205                1210                1215

Asp Asp Arg Lys Ser Asn Arg Ser Tyr Thr Ser Arg Lys Asp Arg
1220                1225                1230

Glu Arg Phe Arg Glu Glu Glu Val Glu Glu Pro Lys Val Glu Val
1235                1240                1245

Ala Pro Leu Val Pro Ser Ala Asn Arg Trp Val Pro Lys Ser Lys
1250                1255                1260

Met Lys Lys Thr Glu Val Lys Leu Ala Pro Asp Gly Thr Glu Leu
1265                1270                1275

Tyr Asp Ala Glu Glu Ala Ser Arg Lys Met Lys Ser Leu Leu Asn
1280                1285                1290

Lys Leu Thr Leu Glu Met Phe Glu Pro Ile Ser Asp Asp Ile Met
1295                1300                1305

Lys Ile Ala Asn Gln Ser Arg Trp Glu Glu Lys Gly Glu Thr Leu
1310                1315                1320

Lys Ile Val Ile Gln Gln Ile Phe Asn Lys Ala Cys Asp Glu Pro
1325                1330                1335

His Trp Ser Ser Met Tyr Ala Gln Leu Cys Gly Lys Val Val Lys
1340                1345                1350

Asp Leu Asp Asp Ser Ile Lys Asp Ser Glu Thr Pro Asp Lys Thr
1355                1360                1365

Gly Ser His Leu Val Leu His Tyr Leu Val Gln Arg Cys Gln Thr
1370                1375                1380

Glu Phe Gln Thr Gly Trp Thr Asp Gln Leu Pro Thr Asn Glu Asp
1385                1390                1395

Gly Thr Pro Leu Gln Pro Glu Met Met Ser Asp Glu Tyr Tyr Lys
1400                1405                1410

Met Ala Ala Ala Lys Arg Arg Gly Leu Gly Leu Val Arg Phe Ile
1415                1420                1425

Gly Phe Leu Tyr Arg Ser Asn Leu Leu Thr Ser Arg Met Val Phe
1430                1435                1440

Phe Cys Phe Lys Arg Leu Met Lys Asp Ile Gln Asn Ser Pro Thr
1445                1450                1455

Glu Asp Thr Leu Glu Ser Val Cys Glu Leu Leu Glu Thr Ile Gly
1460                1465                1470

Glu Gln Phe Glu Gly Ala Arg Ile Gln Val Thr Ala Glu Ala Val
1475                1480                1485

Ile Glu Gly Ser Ser Leu Leu Asp Thr Leu Phe Asp Gln Ile Lys
1490                1495                1500

Asn Val Ile Glu Asn Gly Asp Ile Ser Ser Arg Ile Lys Phe Lys
1505                1510                1515

Leu Ile Asp Ile Val Glu Leu Arg Glu Lys Arg Asn Trp Asn Ser
```

```
              1520                1525                1530
Lys Asn Lys Asn Asp Gly Pro Lys Thr Ile Ala Gln Ile His Glu
    1535                1540                1545

Glu Glu Ala Leu Lys Arg Ala Leu Glu Glu Arg Glu Arg Glu Arg
    1550                1555                1560

Asp Arg His Gly Ser Arg Gly Gly Ser Arg Arg Met Asn Ser Glu
    1565                1570                1575

Arg Asn Ser Ser Arg Arg Asp Phe Ser Ser His Ser His Ser His
    1580                1585                1590

Asn Gln Asn Arg Asp Gly Phe Thr Thr Thr Arg Ser Ser Ser Val
    1595                1600                1605

Arg Tyr Ser Glu Pro Lys Lys Glu Glu Gln Ala Pro Thr Pro Thr
    1610                1615                1620

Lys Ser Ser Gly Gly Ala Ala Asn Met Phe Asp Ala Leu Met Asp
    1625                1630                1635

Ala Glu Asp Asp
    1640

<210> SEQ ID NO 4
<211> LENGTH: 1779
<212> TYPE: DNA
<213> ORGANISM: Kluyveromyces lactis

<400> SEQUENCE: 4
atgtctgata ttactgaaaa aactgctgag caattggaaa acttgcagat caacgatgat      60
cagcaaccag ctcaatctgc cagtgctcca tccacttctg cttctgaaag cgaagcttct     120
tctgtttcta aggttgaaaa caacaacgct tcattgtacg ttggtgaatt ggatccaaac     180
attactgaag cattgttgta cgatgtgttt tcaccattgg gtccaatttc ctcgatccgt     240
gtttgtcgtg atgccgtcac caaggcttcg ttaggttacg cttacgttaa ctatactgat     300
tacgaagctg taagaaagc tattcaagaa ttgaactatg ctgaaatcaa cggtagacca     360
tgtagaatta tgtggtccga acgtgaccca gctatcagaa agaagggttc tggtaacatt     420
ttcatcaaga acttgcaccc agccattgac aacaaggctt tgcatgaaac tttctccact     480
ttcggtgaag tcttgtcttg taaagttgct ttagatgaga atggaaactc tagaggcttc     540
ggtttcgttc atttcaagga agaatccgat gctaaggatg ctattgaagc cgtcaacggt     600
atgttgatga acggtttgga agtttacgtt gccatgcacg ttccaagaa ggaccgtatc     660
tccaagttgg aagaagccaa ggctaacttc accaacattt acgtcaagaa cattgacgtt     720
gaaaccactg acgaagagtt cgaacagttg ttctcccaat acggtgaaat tgtctctgct     780
gctttggaaa aggatgctga gggtaagcca aagggtttcg gtttcgttaa ctttgttgac     840
cacaacgccg ctgccaaggc cgttgaagag ttgaacggta aggaattcaa gtctcaagct     900
tgtacgttg cagagctca aaagaagtac gaacgtgctg aagaattgaa gaaacaatac     960
gaacaatacc gtttggaaaa attggctaag ttccaaggtg ttaacttgtt catcaagaac    1020
ttggacgatt ccatcgatga cgaaaaattg aaggaagaat cgccccata cggtaccatc    1080
acctctgcta gagtcatgag agaccaagag ggtaactcta agggtttcgg tttcgttgt    1140
ttctcttctc cagaagaagc taccaaggct atgaccgaaa gaaccaaca aattgttgcc    1200
ggtaagccat tgtacgttgc cattgctcaa gaaaaggatg tcagaagatc ccaattggct    1260
caacaaattc aagccagaaa ccaaatcaga ttccaacaac agcaacaaca acaagctgct    1320
gccgctgctg ctggtatgcc aggccaatac atgccacaaa tgttctatgg tgttatggcc    1380
```

-continued

```
ccaagaggtt tcccaggtcc aaacccaggt atgaacggcc caatgggtgc cggtattcca      1440
aagaacggta tggtcccacc accacaacaa tttgctggta gaccaaacgg tccaatgtac      1500
caaggtatgc cacctcaaaa ccaattccca agacaccaac aacaacacta catccaacaa      1560
caaaagcaaa gacaagcctt gggtgaacaa ttgtacaaga aggtcagtgc caagattgac      1620
gacgaaaacg ccgctggtaa gatcaccggt atgatcttgg atctaccacc acagcaagtc      1680
atccaattgt tggacaacga cgaacaattt gaacagcaat ccaagaagc cttagctgct      1740 tacgaaaact tcaagaagga caagaagct caagcttaa                              1779

<210> SEQ ID NO 5
<211> LENGTH: 3066
<212> TYPE: DNA
<213> ORGANISM: Kluyveromyces lactis

<400> SEQUENCE: 5
atgggcgaac ctacatccga tcagcaacca gctgttgaag ctccagttgt gcaggaggag        60
acaaccagtt ctccgcaaaa aaacagtgga tatgtcaaga atactgctgg aagcggtgct       120
cctagaaatg ggaaatatga tggtaacagg aagaactcta ggccttataa ccaaagaggt       180
aacaacaaca ataataatgg ttcttcctcg aataagcact atcaaaagta taaccaacca       240
gcgtacggta tttctgcggg atacattccg aactacggcg tatcggcaga gtacaaccct       300
ctgtactata accagtacca acagcagcaa cagctgtacg ctgctgctta ccagactcca       360
atgagcggac aaggttatgt ccccccagta gtgtctccag ctgctgtttc agctaaacca       420
gcgaaggttg agattactaa caagtctggt gaacacatag atattgcttc cattgctcat       480
ccacatactc attctcattc tcaatctcat tcgcgtgcag ttccagtagt gtcgcctcca       540
gctaacgtta ccgtcgctgc tgctgtatca tcctctgtgt ctccatcagc ttctccagct       600
gtcaaagtac agagccctgc tgctaatggt aaggaacaat ctccagctaa gcctgaagaa       660 ccaagaagg acactttaat tgtgaacgat ttcttggaac aagttaaaag acgcaaggct       720
gctttagctg ctaagaaggc tgtcgaagag aagggtcctg aggaaccgaa ggaatctgtc       780
gttggaactg acactgatgc aagcgttgat actaagacag gcctacagc cactgaatct       840 gccaagtctg aagaagctca atcagaatca caagaaaaga ctaaggaaga ggctccagct       900
gagccaaaac cattgacttt ggccgaaaaa ttgagactta gaggatgga agctgcaaag       960 caagcttctg ctaagaccga ggaactaaag actgaagaat ctaagcctga gaaacaaag      1020 accgaggagc taaagactga gaatctaag cctgaagaaa caagaccga ggagctaaag      1080 actgaagaaa caagagtccga ggaactaaag actgaagaac ctaaggcgga gaatcaaag      1140 gcggaagaac caaagcctga gaaccaaag accgaggaac cgacgactga acaaccaaag      1200
tcagatgaac caaagtcgga gaatcaaaa actgaagagc caaaaccga ggtattaaag      1260 actgaagaac caaaatcgga gaatcaaag cctgcagaac caagactga gaaacagca       1320 actgaagaaa cagcaactga agcaaacgcc gaagaaggtg aaccggctcc tgctggtccc      1380
gttgaaactc ctgctgatgt tgaaacaaaa cctcgagaag aggctgaagt tgaagacgat      1440
ggaaagatta ccatgaccga tttcctacag aagttgaaag aggtttctcc agttgatgat      1500
atttattcct tccaataccc aagtgacatt acgcctccaa atgatagata taaaaagaca      1560
agcattaaat atgcatacgg acctgatttc ttgtatcagt tcaaagaaaa ggtcgatgtt      1620
aaatacgatc cagcgtggat ggctgaaatg acgagtaaaa ttgtcatccc tcctaagaag      1680
```

-continued

```
cctggttcaa gcggaagagg cgaagataga tttagtaagg gtaaggttgg atctctaaga      1740
agtgaaggca gatcgggttc caggtccaac tcgaagaaga agtcaaagag ggatgataga      1800
aaatctaata gatcatacac ttccagaaag gaccgtgaaa gattcagaga ggaagaagtc      1860
gaagagccaa aggttgaggt tgccccattg gtcccaagtg ctaatagatg ggttcctaaa      1920
tctaagatga agaaaacaga agtcaagtta gctccagacg gaacagaact ttacgacgcg      1980
gaagaagcat caagaaagat gaagtcattg ctgaataaat tgacattaga aatgttcgaa      2040
cctatttctg atgatatcat gaagatcgct aaccaatcta gatgggaaga aaagggtgag      2100
actttgaaga ttgtcatcca acaaattttc aataaggcct gcgatgaacc tcattggtca      2160
tcaatgtacg cgcaattatg tggtaaggtc gttaaagact tagatgatag cattaaagac      2220
tcagaaaccc cagataagac tggttctcac ttggttttgc attacttagt ccaaagatgt      2280
caaactgaat tccaaacagg atggactgat caactaccta caaacgaaga cggtactcct      2340
ctacaacctg aaatgatgtc cgatgaatac tataagatgg ctgccgctaa gagaagaggt      2400
ttgggtttgg ttcgtttcat tggtttcttg taccgttcga acttattgac ttccagaatg      2460
gtcttcttct gtttcaagag actaatgaag gatattcaaa actctcctac tgaagatact      2520
ctagagtctg tatgtgaact tttgaaaaca attggtgaac agttcgaagg tgctcgtatt      2580
caagttactg cagaagctgt cattgagggt tcaagcttgc tagacacact attcgaccaa      2640
ataaagaacg tgatcgaaaa tggtgacatc tccagcagaa tcaagtttaa gttgatcgac      2700
attgtcgaac taagagaaaa gaggaactgg aatagtaaaa ataagaacga tggtccaaag      2760
accattgctc aaattcacga agaagaagcc ttgaagaggg ctttggagga aagagaaaga      2820
gaaagagatc gccatgggtc cagaggtggt tccagacgta tgaatagcga gagaaactct      2880
tctagaagag atttctcctc tcattctcac agtcacaatc aaaatagaga cggtttcact      2940
actaccagat cgtcatcagt gagatattct gagccaaaga aggaagaaca agctccaact      3000
ccaactaaat cttctggtgg cgctgccaac atgtttgatg cattgatgga tgccgaagat      3060
gattaa                                                                3066

<210> SEQ ID NO 6
<211> LENGTH: 20
<212> TYPE: DNA
<213> ORGANISM: Artificial sequence
<220> FEATURE:
<223> OTHER INFORMATION: optimized KleIF4G gRNA sequence

<400> SEQUENCE: 6 cggttttca aagcagatat                                                   20

<210> SEQ ID NO 7
<211> LENGTH: 62
<212> TYPE: DNA
<213> ORGANISM: Artificial sequence
<220> FEATURE:
<223> OTHER INFORMATION: primer PF1

<400> SEQUENCE: 7 cggttttca aagcagatat gttttagagc tagaaatagc aagttaaaat aaggctagtc      60
cg                                                                     62

<210> SEQ ID NO 8
<211> LENGTH: 50
<212> TYPE: DNA
<213> ORGANISM: Artificial sequence
```

<220> FEATURE:
<223> OTHER INFORMATION: primer PR1

<400> SEQUENCE: 8
gctctaaaac atatctgctt tgaaaaaccg aaagtcccat tcgccacccg            50

<210> SEQ ID NO 9
<211> LENGTH: 72
<212> TYPE: DNA
<213> ORGANISM: Artificial sequence
<220> FEATURE:
<223> OTHER INFORMATION: primer PF2

<400> SEQUENCE: 9
gagctcggta cccggggatc tctagagat aataaaattt caacctttaa gccattgaat   60
tttaccatta cg                                                      72

<210> SEQ ID NO 10
<211> LENGTH: 57
<212> TYPE: DNA
<213> ORGANISM: Artificial sequence
<220> FEATURE:
<223> OTHER INFORMATION: primer PR2

<400> SEQUENCE: 10
gccaagcttg catgcctgca ggtcgacgat cttgttagta atctcaacct tcgctgg     57

<210> SEQ ID NO 11
<211> LENGTH: 20
<212> TYPE: DNA
<213> ORGANISM: Artificial sequence
<220> FEATURE:
<223> OTHER INFORMATION: primer pMD18-F

<400> SEQUENCE: 11
atcgtcgacc tgcaggcatg                                              20

<210> SEQ ID NO 12
<211> LENGTH: 20
<212> TYPE: DNA
<213> ORGANISM: Artificial sequence
<220> FEATURE:
<223> OTHER INFORMATION: primer pMD18-R

<400> SEQUENCE: 12
atctctagag gatccccggg                                              20

<210> SEQ ID NO 13
<211> LENGTH: 22
<212> TYPE: DNA
<213> ORGANISM: Artificial sequence
<220> FEATURE:
<223> OTHER INFORMATION: primer PF3

<400> SEQUENCE: 13
atgggcgaac ctacatccga tc                                           22

<210> SEQ ID NO 14
<211> LENGTH: 29
<212> TYPE: DNA
<213> ORGANISM: Artificial sequence
<220> FEATURE:
<223> OTHER INFORMATION: primer PR3

<400> SEQUENCE: 14

```
atctgctttg aaaaaccgct ctttctctc                                         29
```

<210> SEQ ID NO 15
<211> LENGTH: 60
<212> TYPE: DNA
<213> ORGANISM: Artificial sequence
<220> FEATURE:
<223> OTHER INFORMATION: primer PF4

<400> SEQUENCE: 15

```
agagagaaag agcggttttt caaagcagat ccacacacca tagcttcaaa atgtttctac      60
```

<210> SEQ ID NO 16
<211> LENGTH: 66
<212> TYPE: DNA
<213> ORGANISM: Artificial sequence
<220> FEATURE:
<223> OTHER INFORMATION: primer PR4

<400> SEQUENCE: 16

```
tggttgctga tcggatgtag gttcgcccat cttagattag attgctatgc tttctttcta      60
atgagc                                                                 66
```

<210> SEQ ID NO 17
<211> LENGTH: 56
<212> TYPE: DNA
<213> ORGANISM: Artificial sequence
<220> FEATURE:
<223> OTHER INFORMATION: primer PF5

<400> SEQUENCE: 17

```
agagagaaag agcggttttt caaagcagat agacgcgaat ttttcgaaga agtacc          56
```

<210> SEQ ID NO 18
<211> LENGTH: 89
<212> TYPE: DNA
<213> ORGANISM: Artificial sequence
<220> FEATURE:
<223> OTHER INFORMATION: primer PR5

<400> SEQUENCE: 18

```
agcttcaaca gctggttgct gatcggatgt aggttcgccc attgttttat atttgttgta      60
aaaagtagat aattacttcc ttgatgatc                                        89
```

<210> SEQ ID NO 19
<211> LENGTH: 51
<212> TYPE: DNA
<213> ORGANISM: Artificial sequence
<220> FEATURE:
<223> OTHER INFORMATION: primer PF6

<400> SEQUENCE: 19

```
agagagaaag agcggttttt caaagcagat gagcctgtcc aagcaaatgc c               51
```

<210> SEQ ID NO 20
<211> LENGTH: 62
<212> TYPE: DNA
<213> ORGANISM: Artificial sequence
<220> FEATURE:
<223> OTHER INFORMATION: primer PR6

<400> SEQUENCE: 20

```
tggttgctga tcggatgtag gttcgcccat ttttaatgtt acttctcttg cagttaggga      60
ac                                                                     62
```

<210> SEQ ID NO 21
<211> LENGTH: 56
<212> TYPE: DNA
<213> ORGANISM: Artificial sequence
<220> FEATURE:
<223> OTHER INFORMATION: primer PF7

<400> SEQUENCE: 21
agagagaaag agcggttttt caaagcagat gttcctcatc actagaagcc gaactg        56

<210> SEQ ID NO 22
<211> LENGTH: 89
<212> TYPE: DNA
<213> ORGANISM: Artificial sequence
<220> FEATURE:
<223> OTHER INFORMATION: primer PR7

<400> SEQUENCE: 22
agcttcaaca gctggttgct gatcggatgt aggttcgccc attttttatta attcttgatc        60 gattttttg ttatttctga agtaactct        89

<210> SEQ ID NO 23
<211> LENGTH: 20
<212> TYPE: DNA
<213> ORGANISM: Artificial sequence
<220> FEATURE:
<223> OTHER INFORMATION: KLTDH3 gRNA sequenc

<400> SEQUENCE: 23
cttgttgcta agaactaaag        20

<210> SEQ ID NO 24
<211> LENGTH: 20
<212> TYPE: DNA
<213> ORGANISM: Artificial sequence
<220> FEATURE:
<223> OTHER INFORMATION: KLTDH3 gRNA sequenc

<400> SEQUENCE: 24
ctctgaaaga gttgtcgatt        20

<210> SEQ ID NO 25
<211> LENGTH: 50
<212> TYPE: DNA
<213> ORGANISM: Artificial sequence
<220> FEATURE:
<223> OTHER INFORMATION: primer PF8

<400> SEQUENCE: 25
cttgttgcta agaactaaag gttttagagc tagaaatagc aagttaaaat        50

<210> SEQ ID NO 26
<211> LENGTH: 50
<212> TYPE: DNA
<213> ORGANISM: Artificial sequence
<220> FEATURE:
<223> OTHER INFORMATION: primer PR8

<400> SEQUENCE: 26
gctctaaaac ctttagttct tagcaacaag aaagtcccat tcgccacccg        50

<210> SEQ ID NO 27
<211> LENGTH: 50
<212> TYPE: DNA

<213> ORGANISM: Artificial sequence
<220> FEATURE:
<223> OTHER INFORMATION: primer PF9

<400> SEQUENCE: 27
ctctgaaaga gttgtcgatt gttttagagc tagaaatagc aagttaaaat    50

<210> SEQ ID NO 28
<211> LENGTH: 50
<212> TYPE: DNA
<213> ORGANISM: Artificial sequence
<220> FEATURE:
<223> OTHER INFORMATION: primer PR9

<400> SEQUENCE: 28
gctctaaaac aatcgacaac tctttcagag aaagtcccat tcgccacccg    50

<210> SEQ ID NO 29
<211> LENGTH: 55
<212> TYPE: DNA
<213> ORGANISM: Artificial sequence
<220> FEATURE:
<223> OTHER INFORMATION: primer PF10

<400> SEQUENCE: 29
gagctcggta cccggggatc tctagagat catccactcc atcaccgcta cccaa    55

<210> SEQ ID NO 30
<211> LENGTH: 52
<212> TYPE: DNA
<213> ORGANISM: Artificial sequence
<220> FEATURE:
<223> OTHER INFORMATION: primer PR10

<400> SEQUENCE: 30
gccaagcttg catgcctgca ggtcgacgat caacgtcccc atctacaaga gc    52

<210> SEQ ID NO 31
<211> LENGTH: 20
<212> TYPE: DNA
<213> ORGANISM: Artificial sequence
<220> FEATURE:
<223> OTHER INFORMATION: primer pMD18-F

<400> SEQUENCE: 31
atcgtcgacc tgcaggcatg    20

<210> SEQ ID NO 32
<211> LENGTH: 20
<212> TYPE: DNA
<213> ORGANISM: Artificial sequence
<220> FEATURE:
<223> OTHER INFORMATION: primer pMD18-R

<400> SEQUENCE: 32
atctctagag gatccccggg    20

<210> SEQ ID NO 33
<211> LENGTH: 73
<212> TYPE: DNA
<213> ORGANISM: Artificial sequence
<220> FEATURE:
<223> OTHER INFORMATION: primer PF11

<400> SEQUENCE: 33
gatgcattga tggatgccga agatgattaa agaggttgat gtaattgata ttttcctgat    60

-continued

```
aaaattacta ttg                                                      73

<210> SEQ ID NO 34
<211> LENGTH: 103
<212> TYPE: DNA
<213> ORGANISM: Artificial sequence
<220> FEATURE:
<223> OTHER INFORMATION: primer PR11

<400> SEQUENCE: 34
agctggttgc tgatcggatg taggttcgcc agatccacct ccttccacgt ttgttggtct   60
tgatccacct ccaccgttct tagcaacaag ttcgaccaaa tcg                    103

<210> SEQ ID NO 35
<211> LENGTH: 22
<212> TYPE: DNA
<213> ORGANISM: Artificial sequence
<220> FEATURE:
<223> OTHER INFORMATION: primer PF12

<400> SEQUENCE: 35
ggcgaaccta catccgatca gc                                            22

<210> SEQ ID NO 36
<211> LENGTH: 27
<212> TYPE: DNA
<213> ORGANISM: Artificial sequence
<220> FEATURE:
<223> OTHER INFORMATION: primer PR12

<400> SEQUENCE: 36
ttaatcatct tcggcatcca tcaatgc                                       27

<210> SEQ ID NO 37
<211> LENGTH: 17
<212> TYPE: DNA
<213> ORGANISM: Artificial sequence
<220> FEATURE:
<223> OTHER INFORMATION: primer M13-F

<400> SEQUENCE: 37
gtaaaacgac ggccagt                                                  17

<210> SEQ ID NO 38
<211> LENGTH: 17
<212> TYPE: DNA
<213> ORGANISM: Artificial sequence
<220> FEATURE:
<223> OTHER INFORMATION: primer M13-R

<400> SEQUENCE: 38
caggaaacag ctatgac                                                  17

<210> SEQ ID NO 39
<211> LENGTH: 52
<212> TYPE: DNA
<213> ORGANISM: Artificial sequence
<220> FEATURE:
<223> OTHER INFORMATION: primer PF13

<400> SEQUENCE: 39
gagctcggta cccggggatc ctctagagat gaagctttga tgactaccgt tc           52

<210> SEQ ID NO 40
```

```
<211> LENGTH: 55
<212> TYPE: DNA
<213> ORGANISM: Artificial sequence
<220> FEATURE:
<223> OTHER INFORMATION: primer PR13

<400> SEQUENCE: 40
gccaagcttg catgcctgca ggtcgacgat gtctattgta tcggaagaac tgtca       55

<210> SEQ ID NO 41
<211> LENGTH: 20
<212> TYPE: DNA
<213> ORGANISM: Artificial sequence
<220> FEATURE:
<223> OTHER INFORMATION: primer pMD18-F

<400> SEQUENCE: 41
atcgtcgacc tgcaggcatg                                              20

<210> SEQ ID NO 42
<211> LENGTH: 20
<212> TYPE: DNA
<213> ORGANISM: Artificial sequence
<220> FEATURE:
<223> OTHER INFORMATION: primer pMD18-R

<400> SEQUENCE: 42
atctctagag gatccccggg                                              20

<210> SEQ ID NO 43
<211> LENGTH: 65
<212> TYPE: DNA
<213> ORGANISM: Artificial sequence
<220> FEATURE:
<223> OTHER INFORMATION: primer PF14

<400> SEQUENCE: 43
gatgcattga tggatgccga agatgattaa attactcttt taagttaacg aacgcttttg  60
atgag                                                              65

<210> SEQ ID NO 44
<211> LENGTH: 130
<212> TYPE: DNA
<213> ORGANISM: Artificial sequence
<220> FEATURE:
<223> OTHER INFORMATION: primer PR14

<400> SEQUENCE: 44
agctggttgc tgatcggatg taggttcgcc agatccacct ccttccacgt tgttggtct   60 tgatccacct ccaccagcaa cgtgctcaac taagtcaacg acccctttcag agtaaccgta 120 ttcgttatcg                                                         130

<210> SEQ ID NO 45
<211> LENGTH: 22
<212> TYPE: DNA
<213> ORGANISM: Artificial sequence
<220> FEATURE:
<223> OTHER INFORMATION: primer PF15

<400> SEQUENCE: 45
ggcgaaccta catccgatca gc                                           22

<210> SEQ ID NO 46
<211> LENGTH: 27
```

```
<212> TYPE: DNA
<213> ORGANISM: Artificial sequence
<220> FEATURE:
<223> OTHER INFORMATION: primer PR15

<400> SEQUENCE: 46
ttaatcatct tcggcatcca tcaatgc                                    27

<210> SEQ ID NO 47
<211> LENGTH: 17
<212> TYPE: DNA
<213> ORGANISM: Artificial sequence
<220> FEATURE:
<223> OTHER INFORMATION: primer M13-F

<400> SEQUENCE: 47
gtaaaacgac ggccagt                                               17

<210> SEQ ID NO 48
<211> LENGTH: 17
<212> TYPE: DNA
<213> ORGANISM: Artificial sequence
<220> FEATURE:
<223> OTHER INFORMATION: primer M13-R

<400> SEQUENCE: 48
caggaaacag ctatgac                                               17

<210> SEQ ID NO 49
<211> LENGTH: 26
<212> TYPE: DNA
<213> ORGANISM: Artificial sequence
<220> FEATURE:
<223> OTHER INFORMATION: primer KlTDH3-1-ClCF1

<400> SEQUENCE: 49
cttctactgc tccaatgttc gtcgtt                                     26

<210> SEQ ID NO 50
<211> LENGTH: 25
<212> TYPE: DNA
<213> ORGANISM: Artificial sequence
<220> FEATURE:
<223> OTHER INFORMATION: primer KlTDH3-2-ClCF1

<400> SEQUENCE: 50
ttaacgaaga caagtacaac ggtga                                      25

<210> SEQ ID NO 51
<211> LENGTH: 25
<212> TYPE: DNA
<213> ORGANISM: Artificial sequence
<220> FEATURE:
<223> OTHER INFORMATION: primer KleIF4G-ClCR2

<400> SEQUENCE: 51
ttctcttcga cagccttctt agcag                                      25

<210> SEQ ID NO 52
<211> LENGTH: 20
<212> TYPE: DNA
<213> ORGANISM: Artificial sequence
<220> FEATURE:
<223> OTHER INFORMATION: KlPab1 gRNA sequence

<400> SEQUENCE: 52
```

```
tgcttacgaa aacttcaaga                                                20
```

<210> SEQ ID NO 53
<211> LENGTH: 62
<212> TYPE: DNA
<213> ORGANISM: Artificial sequence
<220> FEATURE:
<223> OTHER INFORMATION: primer PF16

<400> SEQUENCE: 53

```
tgcttacgaa aacttcaaga gttttagagc tagaaatagc aagttaaaat aaggctagtc    60
cg                                                                   62
```

<210> SEQ ID NO 54
<211> LENGTH: 50
<212> TYPE: DNA
<213> ORGANISM: Artificial sequence
<220> FEATURE:
<223> OTHER INFORMATION: primer PR16

<400> SEQUENCE: 54

```
gctctaaaac tcttgaagtt ttcgtaagca aaagtcccat tcgccacccg               50
```

<210> SEQ ID NO 55
<211> LENGTH: 55
<212> TYPE: DNA
<213> ORGANISM: Artificial sequence
<220> FEATURE:
<223> OTHER INFORMATION: primer PF17

<400> SEQUENCE: 55

```
gagctcggta cccggggatc ctctagagat ccggtaagcc attgtacgtt gccat         55
```

<210> SEQ ID NO 56
<211> LENGTH: 55
<212> TYPE: DNA
<213> ORGANISM: Artificial sequence
<220> FEATURE:
<223> OTHER INFORMATION: primer PR17

<400> SEQUENCE: 56

```
gccaagcttg catgcctgca ggtcgacgat cagtataccg tccatgttga tgact         55
```

<210> SEQ ID NO 57
<211> LENGTH: 20
<212> TYPE: DNA
<213> ORGANISM: Artificial sequence
<220> FEATURE:
<223> OTHER INFORMATION: primer pMD18-F

<400> SEQUENCE: 57

```
atcgtcgacc tgcaggcatg                                                20
```

<210> SEQ ID NO 58
<211> LENGTH: 20
<212> TYPE: DNA
<213> ORGANISM: Artificial sequence
<220> FEATURE:
<223> OTHER INFORMATION: primer pMD18-R

<400> SEQUENCE: 58

```
atctctagag gatccccggg                                                20
```

<210> SEQ ID NO 59
<211> LENGTH: 63

```
<212> TYPE: DNA
<213> ORGANISM: Artificial sequence
<220> FEATURE:
<223> OTHER INFORMATION: primer PF18

<400> SEQUENCE: 59
gatgcattga tggatgccga agatgattaa acttgatttt tgaccttga tcttcatctt    60 gtc                                                                 63

<210> SEQ ID NO 60
<211> LENGTH: 100
<212> TYPE: DNA
<213> ORGANISM: Artificial sequence
<220> FEATURE:
<223> OTHER INFORMATION: primer PR18

<400> SEQUENCE: 60
cttgaacttc atcttgagtt gaacctccac ctccagatcc acctccacca gcttgagctt    60
cttgttcttt tttaaaattc tcgtaagcag ctaaggcttc                         100

<210> SEQ ID NO 61
<211> LENGTH: 93
<212> TYPE: DNA
<213> ORGANISM: Artificial sequence
<220> FEATURE:
<223> OTHER INFORMATION: primer PF19

<400> SEQUENCE: 61
gtggaggttc aactcaagat gaagttcaag gtccacatgc tggtaagtct actgttggtg    60
gaggtggatc tggcgaacct acatccgatc agc                                93

<210> SEQ ID NO 62
<211> LENGTH: 27
<212> TYPE: DNA
<213> ORGANISM: Artificial sequence
<220> FEATURE:
<223> OTHER INFORMATION: primer PR19

<400> SEQUENCE: 62
ttaatcatct tcggcatcca tcaatgc                                       27

<210> SEQ ID NO 63
<211> LENGTH: 17
<212> TYPE: DNA
<213> ORGANISM: Artificial sequence
<220> FEATURE:
<223> OTHER INFORMATION: primer M13-F

<400> SEQUENCE: 63
gtaaaacgac ggccagt                                                  17

<210> SEQ ID NO 64
<211> LENGTH: 17
<212> TYPE: DNA
<213> ORGANISM: Artificial sequence
<220> FEATURE:
<223> OTHER INFORMATION: primer M13-R

<400> SEQUENCE: 64
caggaaacag ctatgac                                                  17

<210> SEQ ID NO 65
<211> LENGTH: 25
<212> TYPE: DNA
```

```
<213> ORGANISM: Artificial sequence
<220> FEATURE:
<223> OTHER INFORMATION: primer KlPAB1-CICF1

<400> SEQUENCE: 65
tctccagaag aagctaccaa ggcta                                    25

<210> SEQ ID NO 66
<211> LENGTH: 25
<212> TYPE: DNA
<213> ORGANISM: Artificial sequence
<220> FEATURE:
<223> OTHER INFORMATION: primer KleIF4G-CICR2

<400> SEQUENCE: 66
ttctcttcga cagccttctt agcag                                    25
```

FUSION PROTEIN COMPRISING A PAB1 ELEMENT AND AN EIF4G ELEMENT AND USE OF THE FUSION PROTEIN FOR IMPROVING PROTEIN SYNTHESIS

TECHNICAL FIELD

The present invention relates to genetic engineering, and particularly to the preparation of novel fusion proteins and their application in improving protein synthesis.

BACKGROUND

Proteins are important molecules in cells, which are involved in almost all functions of cells. Different functions of proteins depend on different sequences and structures. In cells, proteins can act as enzymes to catalyze various biochemical reactions, and can act as signal molecules to coordinate various activities of organisms. Proteins can also support biologic forms, store energy, transport molecules and enable organisms to move. In the field of biomedicine, antibodies of protein types, as targeted protein drugs, are an important means to treat diseases such as cancer.

In cells, the regulation of protein translation plays an important role in various processes, such as coping with external pressure (e.g., nutritional deficiency), cell development, cell differentiation, and so on. Four processes of protein translation include translation initiation, translation elongation (or translated as translation extension), translation termination and ribosome recycling, among which translation initiation is the most regulated process. In the initiation stage of translation, the small ribosomal subunit (40S) binds (tRNA)$_i^{Met}$, and recognizes the 5' terminal of mRNA with the help of various translation initiation factors. The small subunit moves downstream, combines the large ribosomal subunit (60S) at the initiation codon (ATG) to form a complete ribosome, and then enters the stage of translation elongation.

In the rapidly dividing yeast cells, the rate of protein synthesis is approximately 13,000 molecules per second. In vivo, the rate of protein synthesis is limited by the number of ribosomes. The average number of ribosomes in one cell is about 200,000, and the number of mRNA molecules is about 15,000 to 60,000.

At present, commercial products of in-vitro protein expression systems often used in experiments, include *E. coli* systems (*E. coli* extract, ECE), rabbit reticulocyte systems (rabbit reticulocyte lysate, RRL), wheat germ systems (wheat germ extract, WGE), insect systems (insect cell extract, ICE) and humanized systems.

Among the present commercial products of in-vitro protein synthesis systems, the protein yield of a prokaryotic system can reach approximately 0.5 mg/mL, with a cost of about 10 RMB/µg. For eukaryotic systems, the protein yield of a CHO system can reach approximately 0.7 mg/mL, with a cost of about 20 RMB/µg. Therefore, both intracellular protein synthesis systems in nature and artificial extracellular protein synthesis systems have the characteristic of low efficiency and low rate, which greatly limits the application of protein synthesis.

Therefore, there is an urgent need in the field to develop an in-vitro protein synthesis system that can effectively enhance the efficiency of in-vitro protein synthesis.

SUMMARY

The present invention is aimed to provide an in-vitro protein synthesis system that can effectively enhance the efficiency of in-vitro protein synthesis.

A first aspect of the present invention provides a fusion protein, wherein, the fusion protein has a structure represented by the general Formula Ia or Formula Ib:

$$S\text{-}A\text{-}B\text{-}C \quad (Ia)$$

$$S\text{-}C\text{-}B\text{-}A \quad (Ib)$$

wherein,
A is a Pab1 element;
B is none or a linker peptide;
C is an eIF4G element;
S is a signal peptide; and
each "-" is respectively a peptide bond.

In another preferred embodiment, the Formula Ia or Ib corresponds to a structure from the N-terminus to the C-terminus.

In another preferred embodiment, the element A includes a Pab1 sequence of wild-type and a Pab1 sequence of mutant type.

In another preferred embodiment, the Pab1 element is a Pab1 derived from yeast.

In another preferred embodiment, the element A has a sequence as shown in SEQ ID NO.: 1 or an active fragment thereof, or contains a peptide which has a sequence homology of ≥85% (preferably ≥90%; more preferably ≥95%; most preferably ≥97%, such as ≥98%, ≥99%, etc) to the amino acid sequence as shown in SEQ ID NO.: 1 and has the same activity as the sequence of SEQ ID NO.: 1.

In another preferred embodiment, the element C includes an eIF4G sequence of wild-type and an eIF4G sequence of mutant type.

In another preferred embodiment, the eIF4G element is an eIF4G derived from yeast.

In another preferred embodiment, the element C has a sequence as shown in SEQ ID NO.: 2 or an active fragment thereof, or contains a peptide which has a sequence homology of ≥85% (preferably ≥90%; more preferably ≥95%; most preferably ≥97%, such as ≥98%, ≥99%, etc) to the amino acid sequence as shown in SEQ ID NO.: 2 and has the same activity as the sequence of SEQ ID NO.: 2.

In another preferred embodiment, the fusion protein is a recombinant protein, and preferably a recombinant protein expressed by yeast.

In another preferred embodiment, the yeast is selected from the group consisting of: *Kluyveromyces, Saccharomyces cerevisiae*, and the combination thereof.

In another preferred embodiment, the yeast is selected from the group consisting of: *Kluyveromyces lactis, Kluyveromyces marxianus, Kluyveromyces dobzhanskii*, and the combination thereof.

In another preferred embodiment, the element A is a Pab1 protein derived from yeast.

In another preferred embodiment, the element C is an eIF4G protein derived from yeast.

In another preferred embodiment, the peptide linker has a length of 0-50 amino acids, preferably of 10-40 amino acids, and more preferably of 15-25 amino acids.

In another preferred embodiment, the fusion protein is selected from the group consisting of:

(A) a peptide having an amino acid sequence as shown in SEQ ID NO.: 3;

(B) a peptide which has a sequence homology of ≥80% (preferably ≥90%; more preferably ≥95%; most preferably ≥97%, such as ≥98%, ≥99%, etc) to the amino acid sequence as shown in SEQ ID NO.: 3, and the peptide has a function or activity of increasing the efficiency of exogenous protein expression; and (C) a peptide which is formed after any one of the amino acid sequences as shown in SEQ ID NO.: 3 is substituted, deleted or added by 1-15 amino acid residues (preferably, 2-10 amino acid residues, more preferably, 3-8 amino acid residues): and the derived peptide has a function or activity of increasing the efficiency of exogenous protein expression.

In another preferred embodiment, the amino acid sequence of the fusion protein is shown in SEQ ID NO.: 3.

In another preferred embodiment, the fusion protein has one or more characteristics selected from the group consisting of:
(a) improving the efficiency of exogenous protein expression; and (b) improving the efficiency of in-vitro translation.

In another preferred embodiment, the exogenous protein is selected from the group consisting of: luciferin or luciferases (such as firefly luciferase), green fluorescent protein, yellow fluorescent protein, aminoacyl tRNA synthetase, glyceraldehyde-3-phosphate dehydrogenase, catalase, actin, the variable region of antibodies, luciferase mutants or variants, α-amylase, enterocin A, hepatitis C virus (HCV) E2 glycoprotein, insulin precursors, interferon alpha A (IFN-αA), interleukin-1β (IL-1β), lysozyme, serum albumin, single-chain fragment variable (scFv) of antibodies, tranthyretin, tyrosinase, xylanase, and the combination thereof.

A second aspect of the present invention provides an isolated polynucleotide which encodes the fusion protein described in the first aspect of the present invention.

In another preferred embodiment, the polynucleotide is selected from the group consisting of: a DNA sequence and an RNA sequence.

In another preferred embodiment, the DNA sequence is selected from the group consisting of: a genomic sequence and a cDNA sequence.

In another preferred embodiment, the polynucleotide is mRNA or cDNA, and the polynucleotide has a structured represented by Formula II:

A1-C1  (Formula II)

wherein,
A1 is a nucleotide sequence encoding the above-said A element;
C1 is a nucleotide sequence encoding the above-said C element; and
"-" is a linking bond which connects the A1 element and the C1 element.

In another preferred embodiment, the element A1 has a sequence as shown in SEQ ID NO.: 4.

In another preferred embodiment, the element C1 has a sequence as shown in SEQ ID NO.: 5.

A third aspect of the present invention provides a vector which comprises the polynucleotide described in the second aspect of the present invention.

A fourth aspect of the present invention provides a host cell, wherein, the host cell comprises the vector described in the third aspect of the present invention, or the genome of the host cell is integrated with the polynucleotide of the second aspect of the present invention.

In another preferred embodiment, the host cell is formed by transforming the expression vector of the third aspect of the present invention or the polynucleotide of the second aspect of the present invention, followed by homologous recombination, so as that the coding sequence of the fusion protein of the first aspect of the present invention is integrated into the genome or chromosome of the host cell.

In another preferred embodiment, the host cell is selected from the group consisting of: *Kluyveromyces, Saccharomyces cerevisiae*, and the combination thereof.

In another preferred embodiment, the host cell is selected from the group consisting of: *Kluyveromyces lactis, Kluyveromyces marxianus, Kluyveromyces dobzhanskii*, and the combination thereof.

In another preferred embodiment, the host cell is *Kluyveromyces lactis*.

A fifth aspect of the present invention provides an in-vitro protein synthesis system for expressing an exogenous protein, wherein, the reaction system includes:
(i) a yeast-based in-vitro protein synthesis system comprising (a) yeast cell extract; (b) optional polyethylene glycol; (c) optional exogenous sucrose; and (d) an optional solvent, wherein the solvent is water or an aqueous solvent; and
(ii) the fusion protein according to the first aspect of the present invention.

In another preferred embodiment, the reaction system further includes (iii) additionally added eIF4G protein.

In another preferred embodiment, the expression of the eIF4G protein is induced by a constitutive or inducible promoter.

In another preferred embodiment, the constitutive or inducible promoter is derived from yeast.

In another preferred embodiment, the yeast is selected from the group consisting of: *Kluyveromyces, Saccharomyces cerevisiae*, and the combination thereof.

In another preferred embodiment, the constitutive or inducible promoter is selected from the group consisting of: pScTEF1, pScPGK1, pKlTEF1, pKlPGK1, pScADH1, pScTPI1, pScTDH3, pKlADH1, pKlTPI1, pKlTDH3, and the combination thereof.

A sixth aspect of the present invention provides a method for producing the fusion protein described in the first aspect of the present invention, including:
(i) culturing host cells according to the fourth aspect of the present invention under a condition suitable for expression to express the fusion protein according to the first aspect of the present invention; and
(ii) isolating the fusion protein.

A seventh aspect of the present invention provides use of the fusion protein described in the first aspect of the present invention, wherein, the fusion protein is used for preparing an in-vitro protein synthesis system for expressing an exogenous protein. The in-vitro protein synthesis system is used for increasing the expression efficiency of the exogenous protein.

In another preferred embodiment, the reaction system further includes additionally added eIF4G protein.

An eighth aspect of the present invention provides use of the fusion protein described in the first aspect of the present invention, wherein, the fusion protein is used for preparing a preparation which can increase the in-vitro protein synthesis ability of an in-vitro protein synthesis system.

A ninth aspect of the present invention provides a method for expressing an exogenous protein, including:
(i) providing a yeast-based in-vitro protein synthesis system which comprises the fusion protein according to the first aspect of the present invention; and
(ii) incubating the yeast-based in-vitro protein synthesis system in the presence of the template of an exogenous protein to express the exogenous protein under a condition suitable for protein expression.

In another preferred embodiment, the fusion protein is additionally added.

In another preferred embodiment, the fusion protein and other proteins in the yeast-based in-vitro protein synthesis system are extracts derived from the same yeast.

In another preferred embodiment, the method is non-diagnostic and non-therapeutic.

In another preferred embodiment, the step (ii) further comprises a step (iii): detecting the expression activity of the exogenous protein, (Q1); while incubating a wild-type yeast strain under the same condition as that in the step (ii), detecting the activity of the exogenous protein, (Q2); wherein, if Q1 is significantly higher than Q2, it indicates that expression efficiency of the exogenous protein is significantly improved.

In another preferred embodiment, the phrase of "significantly higher than" refers to Q1/Q2≥2, preferably ≥3, and more preferably ≥4.

In another preferred embodiment, the yeast-based in-vitro protein synthesis system is an in-vitro protein synthesis system based on a genetically modified *Kluyveromyces* (preferably an in-vitro protein synthesis system based on *Kluyveromyces lactis*).

In another preferred embodiment, the coding sequence of the exogenous protein is derived from a prokaryotic organism or a eukaryotic organism.

In another preferred embodiment, the coding sequence of the exogenous protein is derived from animal, plant, or pathogen.

In another preferred embodiment, the coding sequence of the exogenous protein is derived from mammal, preferably primate or rodent, including human, mouse, rat, etc.

In another preferred embodiment, the coding sequence of the exogenous protein is selected from the group consisting of: exogenous DNA sequences encoding luciferin or luciferases (such as firefly luciferase), green fluorescent protein, yellow fluorescent protein, aminoacyl tRNA synthetase, glyceraldehyde-3-phosphate dehydrogenase, catalase, actin, the variable region of an antibody, DNA of a luciferase mutant (or translated as luciferase variant), and the combination thereof.

In another preferred embodiment, the exogenous protein is selected from the group consisting of: luciferin or luciferases (such as firefly luciferase), green fluorescent protein, yellow fluorescent protein, aminoacyl tRNA synthetase, glyceraldehyde-3-phosphate dehydrogenase, catalase, actin, the variable region of antibodies, luciferase mutants (or translated as luciferase variants), α-amylase, enterocin A, hepatitis C virus (HCV) E2 glycoprotein, insulin precursors, interferon αA, interleukin-1β, lysozyme, serum albumin, single-chain fragment variable (scFv) of antibodies, tranthyretin, tyrosinase, xylanase, and the combination thereof.

It should be understood that, within the scope of the present invention, the abovementioned technical features of the present invention and technical features specifically described below (e.g., embodiments) can be combined with each other to form a new or preferred technical solution. These combination details will not be described here, due to specification length and words limit.

DETAILED DESCRIPTION

Figure 1:
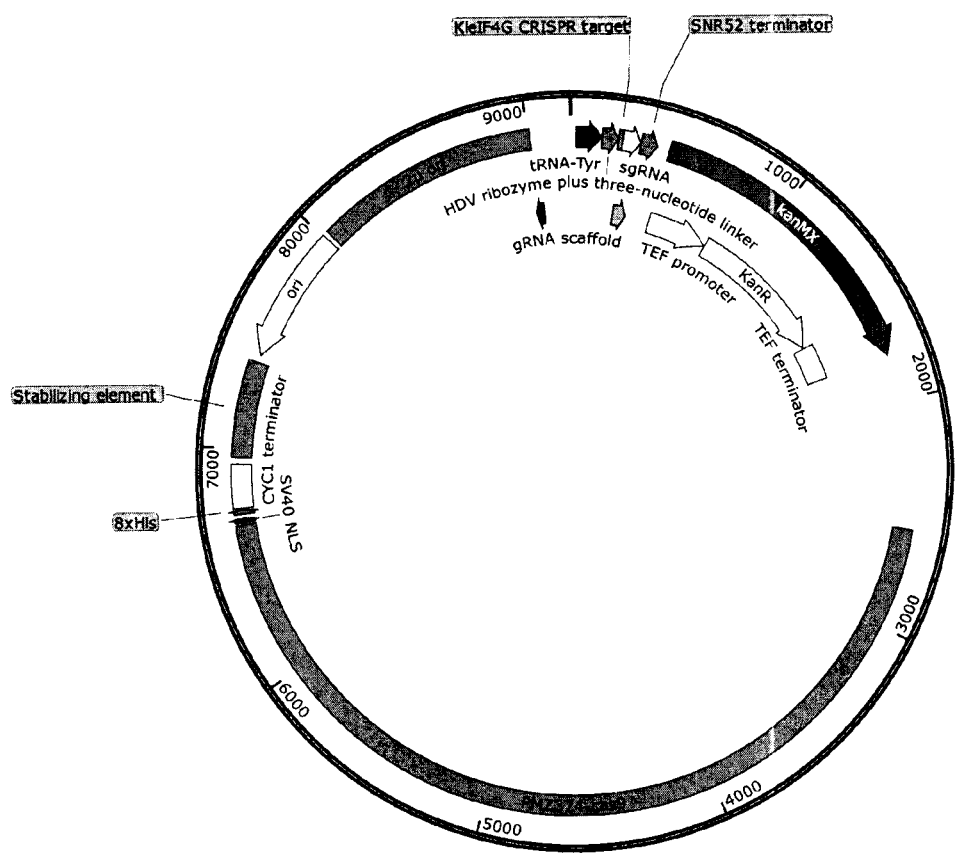
FIG. 1 shows the plasmid map of pKM-CAS1.0-KleIF4G.
Figure 2:
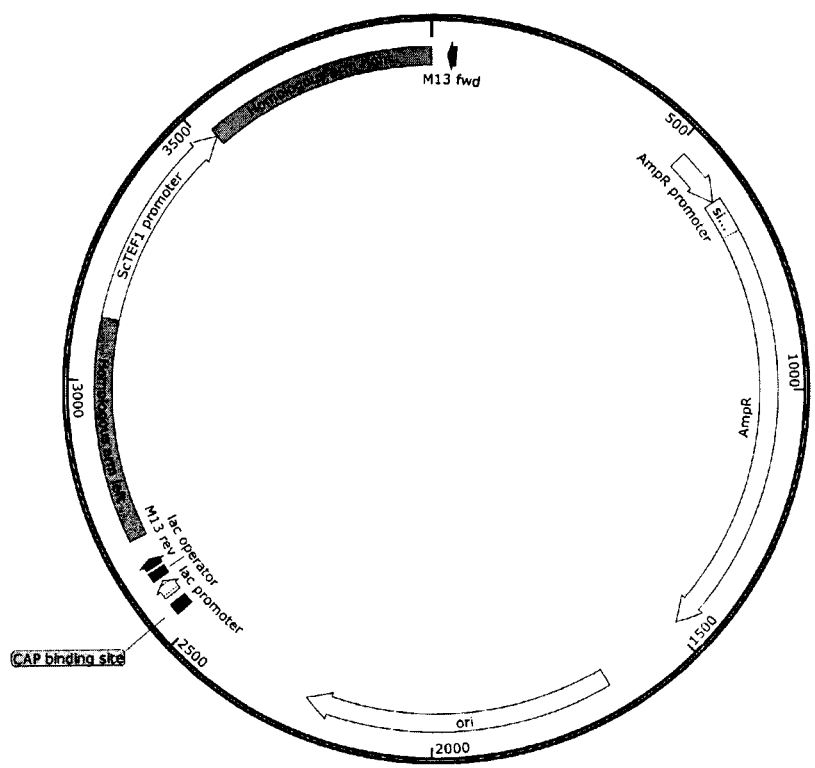
FIG. 2 shows the plasmid map of pKM-pScTEF1-KleIF4G-DD.
Figure 3:
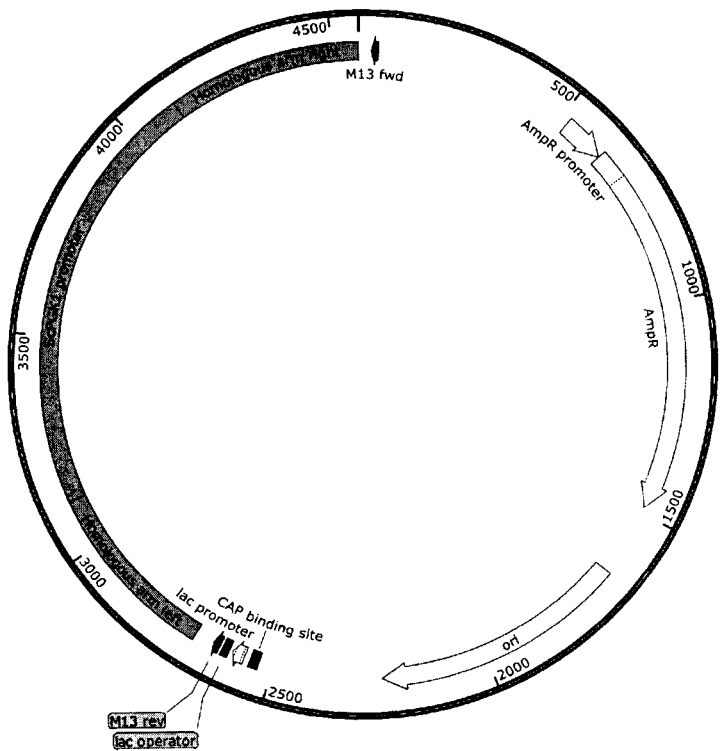
FIG. 3 shows the plasmid map of pKM-pScPGK1-KleIF4G-DD.
Figure 4:
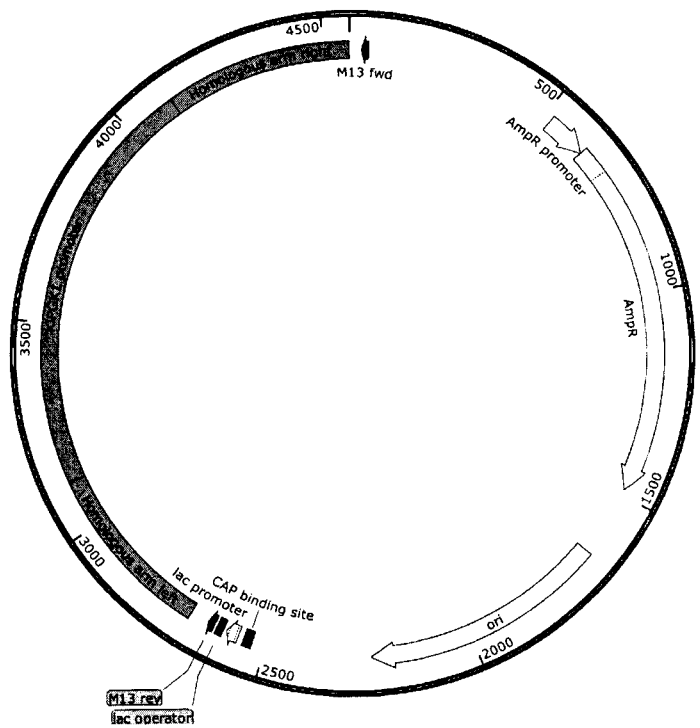
FIG. 4 shows the plasmid map of pKM-pKlTEF1-KleIF4G-DD.
Figure 5:
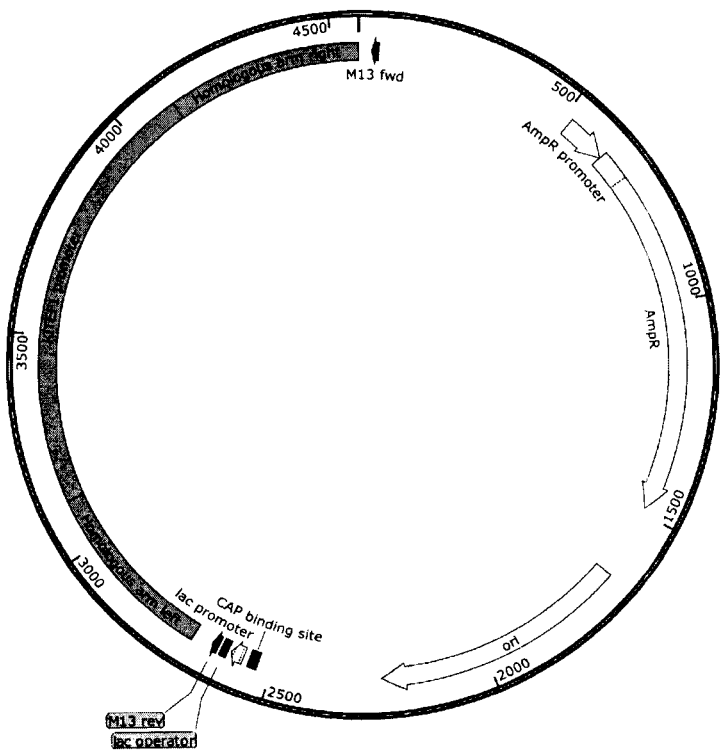
FIG. 5 shows the plasmid map of pKM-pKlPGK1-KleIF4G-DD.

After extensive and in-depth research and through a large number of screenings and explorations, a fusion protein having a structure represented by Formula Ia or Formula Ib was unexpectedly discovered for the first time. The fusion protein of the present invention can greatly improve the in-vitro translation efficiency. In addition, in the present invention, it was also found that inserting a constitutive or inducible promoter (e.g., pScTEF1, pScPGK1, pKlTEF1, pKlPGK1, pScADH1, pScTPI1, pScTDH3, pKlADH1, pKlTPI1, pKlTDH3, etc) in front of the eIF4G element can greatly improve the in-vitro protein synthesis ability.

What's more, inventors of the present invention also found that, while the fusion protein of the present invention improved the in-vitro translation efficiency, the expression level of the element eIF4G of the fusion protein of the present invention did not increase.

Specifically, in a yeast-based in-vitro protein synthesis system containing the fusion protein of the present invention, the value of relative light units referring to the activity of the synthesized luciferase reaches as high as $1.50 \times 10^9$, and the value of relative light units referring to the activity of the synthesized luciferase with a constitutive or inducible promoter being inserted in front of the eIF4G element reaches as high as $1.57 \times 10^9$, which is far higher than the value of relative light units ($4.11 \times 10^8$) referring to the activity of the synthesized luciferase corresponding to a wild-type yeast strain (e.g., Y1140). On this basis, the present inventors completed the present invention.

eIF4G Element

In eukaryotic organisms, various translation initiation factors are involved in the process of protein translation initiation (Table 1). Among them, the eIF4F is responsible for the recognition of "cap structure" and the recruitment of downstream translation initiation factors and ribosomes. The eIF4F consists of three protein subunits: eIF4E, eIF4G and eIF4A. The eIF4E specifically binds to the "cap structure" and anchors the eIF4F to the 5' untranslated region (or 5' UTR; or 5' nontranslated region) of mRNA. The eIF4A is an RNA helicase. The eIF4G, which serves as a scaffold protein during almost the entire translation initiation process and can interact with many translation initiation factors, plays an important role in the recruitment of downstream factors.

TABLE 1

Translation initiation factors in yeast

| Translation Initiation Factor | Subunit | Gene | Protein Length (AA) |
|---|---|---|---|
| eIF1 | | SUI1 | 108 |
| eIF1A | | TIF11 | 153 |
| eIF2 | α | SUI2 | 304 |
| | β | SUI3 | 285 |
| | γ | GCD11 | 527 |
| eIF2B | α | GCN3 | 305 |
| | β | GCD7 | 381 |
| | γ | GCD1 | 578 |
| | δ | GCD2 | 651 |
| | ε | GCD6 | 712 |
| eIF3 | a | RPG1/TIF32 | 964 |
| | b | PRT1 | 763 |
| | c | NIP1 | 812 |
| | g | TIF35 | 274 |
| | i | TIF34 | 347 |
| | j | HCR1 | 265 |
| eIF4A | | TIF1 | 395 |
| | | TIF2 | 395 |
| eIF4B | | TIF3/STM1 | 436 |
| eIF4E | | CDC33 | 213 |
| eIF4G | | TIF4631 | 952 |
| | | TIF4632 | 914 |
| eIF5 | | TIF5 | 405 |
| eIF5B | | FUN12 | 1002 |

In the present invention, by inserting a constitutive or inducible promoter (e.g., pScTEF1, pScPGK1, pKlTEF1, pKlPGK1, pScADH1, pScTPI1, pScTDH3, pKlADH1, pKlTPI1, pKlTDH3 or the like) derived from yeast such as *Saccharomyces cerevisiae, Kluyveromyces* and the like in front of the eIF4G element, the in-vitro protein synthesis ability was improved.

In a preferred embodiment, the eIF4G has a nucleotide sequence as shown in SEQ ID NO.: 5, and an amino acid sequence as shown in SEQ ID NO.: 2.

(SEQ ID NO.: 5)
ATGGGCGAACCTACATCCGATCAGCAACCAGCTGTTGAAGCTCCAGT

TGTGCAGGAGGAGACAACCAGTTCTCCGCAAAAAAACAGTGGATATGTC

AAGAATACTGCTGGAAGCGGTGCTCCTAGAAATGGGAAATATGATGGTA

ACAGGAAGAACTCTAGGCCTTATAACCAAAGAGGTAACAACAACAATAA

TAATGGTTCTTCCTCGAATAAGCACTATCAAAAGTATAACCAACCAGCG

TACGGTGTTTCTGCGGGATACATTCCGAACTACGGCGTATCGGCAGAGT

ACAACCCTCTGTACTATAACCAGTACCAACAGCAGCAACAGCTGTACGC

TGCTGCTTACCAGACTCCAATGAGCGGACAAGGTTATGTCCCCCCAGTA

GTGTCTCCAGCTGCTGTTTCAGCTAAACCAGCGAAGGTTGAGATTACTA

ACAAGTCTGGTGAACACATAGATATTGCTTCCATTGCTCATCCACATAC

TCATTCTCATTCTCAATCTCATTCGCGTGCAGTTCCAGTAGTGTCGCCT

CCAGCTAACGTTACCGTCGCTGCTGCTGTATCATCCTCTGTGTCTCCAT

CAGCTTCTCCAGCTGTCAAAGTACAGAGCCCTGCTGCTAATGGTAAGGA

ACAATCTCCAGCTAAGCCTGAAGAACCAAAGAAGGACACTTTAATTGTG

AACGATTTCTTGGAACAAGTTAAAAGACGCAAGGCTGCTTTAGCTGCTA

AGAAGGCTGTCGAAGAGAAGGGTCCTGAGGAACCGAAGGAATCTGTCGT

TGGAACTGACACTGATGCAAGCGTTGATACTAAGACAGGGCCTACAGCC

ACTGAATCTGCCAAGTCTGAAGAAGCTCAATCAGAATCACAAGAAAAGA

CTAAGGAAGAGGCTCCAGCTGAGCCAAAACCATTGACTTTGGCCGAAAA

ATTGAGACTTAAGAGGATGGAAGCTGCAAAGCAAGCTTCTGCTAAGACC

GAGGAACTAAAGACTGAAGAATCTAAGCCTGAAGAAACAAAGACCGAGG

AGCTAAAGACTGAAGAATCTAAGCCTGAAGAAACAAAGACCGAGGAGCT

AAAGACTGAAGAAACAAAGTCCGAGGAACTAAAGACTGAAGAACCTAAG

GCGGAAGAATCAAAGGCGGAAGAACCAAAGCCTGAAGAACCAAAGACCG

AGGAACCGACGACTGAACAACCAAAGTCAGATGAACCAAAGTCGGAAGA

ATCAAAAACTGAAGAGCCAAAAACCGAGGTATTAAAGACTGAAGAACCA

AAATCGGAAGAATCAAAGCCTGCAGAACCAAAGACTGAAGAAACAGCAA

CTGAAGAAACAGCAACTGAAGCAAACGCCGAAGAAGGTGAACCGGCTCC

TGCTGGTCCCGTTGAAACTCCTGCTGATGTTGAAACAAAACCTCGAGAA

GAGGCTGAAGTTGAAGACGATGGAAAGATTACCATGACCGATTTCCTAC

AGAAGTTGAAAGAGGTTTCTCCAGTTGATGATATTTATTCCTTCCAATA

CCCAAGTGACATTACGCCTCCAAATGATAGATATAAAAAGACAAGCATT

AAATATGCATACGGACCTGATTTCTTGTATCAGTTCAAAGAAAAGGTCG

ATGTTAAATACGATCCAGCGTGGATGGCTGAAATGACGAGTAAAATTGT

CATCCCTCCTAAGAAGCCTGGTTCAAGCGGAAGAGGCGAAGATAGATTT

AGTAAGGGTAAGGTTGGATCTCTAAGAAGTGAAGGCAGATCGGGTTCCA

GGTCCAACTCGAAGAAGAAGTCAAAGAGGGATGATAGAAAATCTAATAG

ATCATACACTTCCAGAAAGGACCGTGAAAGATTCAGAGAGGAAGAAGTC

GAAGAGCCAAAGGTTGAGGTTGCCCCATTGGTCCCAAGTGCTAATAGAT

GGGTTCCTAAATCTAAGATGAAGAAAACAGAAGTCAAGTTAGCTCCAGA

CGGAACAGAACTTTACGACGCGGAAGAAGCATCAAGAAAGATGAAGTCA

TTGCTGAATAAATTGACATTAGAAATGTTCGAACCTATTTCTGATGATA

TCATGAAGATCGCTAACCAATCTAGATGGGAAGAAAAGGGTGAGACTTT

GAAGATTGTCATCCAACAAATTTTCAATAAGGCCTGCGATGAACCTCAT

TGGTCATCAATGTACGCGCAATTATGTGGTAAGGTCGTTAAAGACTTAG

ATGATAGCATTAAAGACTCAGAAACCCCAGATAAGACTGGTTCTCACTT

GGTTTTGCATTACTTAGTCCAAAGATGTCAAACTGAATTCCAAACAGGA

TGGACTGATCAACTACCTACAAACGAAGACGGTACTCCTCTACAACCTG

AAATGATGTCCGATGAATACTATAAGATGGCTGCCGCTAAGAGAAGAGG

TTTGGGTTTGGTTCGTTTCATTGGTTTCTTGTACCGTTCGAACTTATTG

ACTTCCAGAATGGTCTTCTTCTGTTTCAAGAGACTAATGAAGGATATTC

AAAACTCTCCTACTGAAGATACTCTAGAGTCTGTATGTGAACTTTTGGA

AACAATTGGTGAACAGTTCGAAGGTGCTCGTATTCAAGTTACTGCAGAA

GCTGTCATTGAGGGTTCAAGCTTGCTAGACACACTATTCGACCAAATAA

AGAACGTGATCGAAAATGGTGACATCTCCAGCAGAATCAAGTTTAAGTT

GATCGACATTGTCGAACTAAGAGAAAAGAGGAACTGGAATAGTAAAAAT

AAGAACGATGGTCCAAAGACCATTGCTCAAATTCACGAAGAAGAAGCCT

-continued

TGAAGAGGGCTTTGGAGGAAAGAGAAAGAGAAAGAGATCGCCATGGGTC

CAGAGGTGGTTCCAGACGTATGAATAGCGAGAGAAACTCTTCTAGAAGA

GATTTCTCCTCTCATTCTCACAGTCACAATCAAAATAGAGACGGTTTCA

CTACTACCAGATCGTCATCAGTGAGATATTCTGAGCCAAAGAAGGAAGA

ACAAGCTCCAACTCCAACTAAATCTTCTGGTGGCGCTGCCAACATGTTT

GATGCATTGATGGATGCCGAAGATGATTAA (SEQ ID NO.: 2)
MGEPTSDQQPAVEAPVVQEETTSSPQKNSGYVKNTAGSGAPRNGKYD

GNRKNSRPYNQRGNNNNNNGSSSNKHYQKYNQPAYGVSAGYIPNYGVSA

EYNPLYYNQYQQQQQLYAAAYQTPMSGQGYVPPVVSPAAVSAKPAKVEI

TNKSGEHIDIASIAHPHTHSHSQSHSRAVPVVSPPANVTVAAAVSSSVS

PSASPAVKVQSPAANGKEQSPAKPEEPKKDTLIVNDFLEQVKRRKAALA

AKKAVEEKGPEEPKESVVGTDTDASVDTKTGPTATESAKSEEAQSESQE

KTKEEAPAEPKPLTLAEKLRLKRMEAAKQASAKTEELKTEESKPEETKT

EELKTEESKPEETKTEELKTEETKSEELKTEEPKAEESKAEEPKPEEPK

TEEPTTEQPKSDEPKSEESKTEEPKTEVLKTEEPKSEESKPAEPKTEET

ATEETATEANAEEGEPAPAGPVETPADVETKPREEAEVEDDGKITMTDF

LQKLKEVSPVDDIYSFQYPSDITPPNDRYKKTSIKYAYGPDFLYQFKEK

VDVKYDPAWMAEMTSKIVIPPKKPGSSGRGEDRFSKGKVGSLRSEGRSG

SRSNSKKKSKRDDRKSNRSYTSRKDRERFREEEVEEPKVEVAPLVPSAN

RWVPKSKMKKTEVKLAPDGTELYDAEEASRKMKSLLNKLTLEMFEPISD

DIMKIANQSRWEEKGETLKIVIQQIFNKACDEPHWSSMYAQLCGKVVKD

LDDSIKDSETPDKTGSHLVLHYLVQRCQTEFQTGWTDQLPTNEDGTPLQ

PEMMSDEYYKMAAAKRRGLGLVRFIGFLYRSNLLTSRMVFFCFKRLMKD

IQNSPTEDTLESVCELLETIGEQFEGARIQVTAEAVIEGSSLLDTLFDQ

IKNVIENGDISSRIKFKLIDIVELREKRNWNSKNKNDGPKTIAQIHEEE

ALKRALEERERERDRHGSRGGSRRMNSERNSSRRDFSSHSHSHNQNRDG

FTTTRSSSVRYSEPKKEEQAPTPTKSSGGAANMFDALMDAEDD

Pab1 Element (Pab1 Protein)

Pab1 is a 71 kDa RNA-binding protein, which consists of four RNA recognition motif (RRM 1-4) domains and one mademoiselle (MLLE) domain. Each RRM domain comprises two conserved ribonucleoprotein (RNP) structures (RNP1/2) which are responsible for binding to RNA.

In a preferred embodiment, the Pab1 has a nucleotide sequence as shown in SEQ ID NO.: 4 and a protein sequence as shown in SEQ ID NO.: 1.

(SEQ ID NO.: 4)
ATGTCTGATATTACTGAAAAAACTGCTGAGCAATTGGAAAACTTGCA

GATCAACGATGATCAGCAACCAGCTCAATCTGCCAGTGCTCCATCCACT

TCTGCTTCTGAAAGCGAAGCTTCTTCTGTTTCTAAGGTTGAAAACAACA

ACGCTTCATTGTACGTTGGTGAATTGGATCCAAACATTACTGAAGCATT

GTTGTACGATGTGTTTTCACCATTGGGTCCAATTTCCTCGATCCGTGTT

TGTCGTGATGCCGTCACCAAGGCTTCGTTAGGTTACGCTTACGTTAACT

ATACTGATTACGAAGCTGGTAAGAAAGCTATTCAAGAATTGAACTATGC

TGAAATCAACGGTAGACCATGTAGAATTATGTGGTCCGAACGTGACCCA

GCTATCAGAAAGAAGGGTTCTGGTAACATTTTCATCAAGAACTTGCACC

CAGCCATTGACAACAAGGCTTTGCATGAAACTTTCTCCACTTTCGGTGA

AGTCTTGTCTTGTAAAGTTGCTTTAGATGAGAATGGAAACTCTAGAGGC

TTCGGTTTCGTTCATTTCAAGGAAGAATCCGATGCTAAGGATGCTATTG

AAGCCGTCAACGGTATGTTGATGAACGGTTTGGAAGTTTACGTTGCCAT

GCACGTTCCAAAGAAGGACCGTATCTCCAAGTTGGAAGAAGCCAAGGCT

AACTTCACCAACATTTACGTCAAGAACATTGACGTTGAAACCACTGACG

AAGAGTTCGAACAGTTGTTCTCCCAATACGGTGAAATTGTCTCTGCTGC

TTTGGAAAAGGATGCTGAGGGTAAGCCAAAGGGTTTCGGTTTCGTTAAC

TTTGTTGACCACAACGCCGCTGCCAAGGCCGTTGAAGAGTTGAACGGTA

AGGAATTCAAGTCTCAAGCTTTGTACGTTGGCAGAGCTCAAAAGAAGTA

CGAACGTGCTGAAGAATTGAAGAAACAATACGAACAATACCGTTTGGAA

AAATTGGCTAAGTTCCAAGGTGTTAACTTGTTCATCAAGAACTTGGACG

ATTCCATCGATGACGAAAAATTGAAGGAAGAATTCGCCCCATACGGTAC

CATCACCTCTGCTAGAGTCATGAGAGACCAAGAGGGTAACTCTAAGGGT

TTCGGTTTCGTTTGTTTCTCTTCTCCAGAAGAAGCTACCAAGGCTATGA

CCGAAAAGAACCAACAAATTGTTGCCGGTAAGCCATTGTACGTTGCCAT

TGCTCAAAGAAAGGATGTCAGAAGATCCCAATTGGCTCAACAAATTCAA

GCCAGAAACCAAATCAGATTCCAACAACAGCAACAACAACAAGCTGCTG

CCGCTGCTGCTGGTATGCCAGGCCAATACATGCCACAAATGTTCTATGG

TGTTATGGCCCCAAGAGGTTTCCCAGGTCCAAACCCAGGTATGAACGGC

CCAATGGGTGCCGGTATTCCAAAGAACGGTATGGTCCCACCACCACAAC

AATTTGCTGGTAGACCAAACGGTCCAATGTACCAAGGTATGCCACCTCA

AAACCAATTCCCAAGACACCAACAACAACACTACATCCAACAACAAAG

CAAAGACAAGCCTTGGGTGAACAATTGTACAAGAAGGTCAGTGCCAAGA

TTGACGACGAAAACGCCGCTGGTAAGATCACCGGTATGATCTTGGATCT

ACCACCACAGCAAGTCATCCAATTGTTGGACAACGACGAACAATTTGAA

CAGCAATTCCAAGAAGCCTTAGCTGCTTACGAAAACTTCAAGAAGGAAC

AAGAAGCTCAAGCTTAA (SEQ ID NO.: 1)
MSDITEKTAEQLENLQINDDQQPAQSASAPSTSASESEASSVSKVENNN

ASLYVGELDPNITEALLYDVFSPLGPISSIRVCRDAVTKASLGYAYVNY

TDYEAGKKAIQELNYAEINGRPCRIMWSERDPAIRKKGSGNIFIKNLHP

AIDNKALHETFSTFGEVLSCKVALDENGNSRGFGFVHFKEESDAKDAIE

AVNGMLMNGLEVYVAMHVPKKDRISKLEEAKANFTNIYVKNIDVETTDE

EFEQLFSQYGEIVSAALEKDAEGKPKGFGFVNFVDHNAAAKAVEELNGK

EFKSQALYVGRAQKKYERAEELKKQYEQYRLEKLAKFQGVNLFIKNLDD

SIDDEKLKEEFAPYGTITSARVMRDQEGNSKGFGFVCFSSPEEATKAMT

EKNQQIVAGKPLYVAIAQRKDVRRSQLAQQIQARNQIRFQQQQQQAAA

-continued

```
AAAGMPGQYMPQMFYGVMAPRGFPGPNPGMNGPMGAGIPKNGMVPPPQQ

FAGRPNGPMYQGMPPQNQFPRHQQQHYIQQQKQRQALGEQLYKKVSAKI

DDENAAGKITGMILDLPPQQVIQLLDNDEQFEQQFQEALAAYENFKKEQ

EAQA.
```

Fusion Protein

As used herein, terms of "fusion protein of the present invention", "Pab1-eIF4G fusion protein of the present invention" and "Pab1-eIF4G fusion protein" can be used interchangeably, and refer to a fusion protein formed by fusing the Pab1 element and the eIF4G element. In the fusion protein of the present invention, a linker peptide or a flexible linker can or cannot be contained between the Pab1 element and the eIF4G element. In addition, the fusion protein can or cannot contain the starting Met; can or cannot contain a signal peptide; and can or cannot contain a tag sequence (e.g., 6His, etc).

In a preferred embodiment, the fusion protein described in the present invention has an above-described structure of Formula Ia or Formula Ib. Preferably, the fusion protein of the present invention has an amino acid sequence as shown in SEQ ID NO.: 3.

```
                                  (SEQ ID NO.: 3)
MSDITEKTAEQLENLQINDDQQPAQSASAPSTSASESEASSVSKVENNN

ASLYVGELDPNITEALLYDVFSPLGPISSIRVCRDAVTKASLGYAYVNY

TDYEAGKKAIQELNYAEINGRPCRIMWSERDPAIRKKGSGNIFIKNLHP

AIDNKALHETFSTFGEVLSCKVALDENGNSRGFGFVHFKEESDAKDAIE

AVNGMLMNGLEVYVAMHVPKKDRISKLEEAKANFTNIYVKNIDVETTDE

EFEQLFSQYGEIVSAALEKDAEGKPKGFGFVNFVDHNAAAKAVEELNGK

EFKSQALYVGRAQKKYERAEELKKQYEQYRLEKLAKFQGVNLFIKNLDD

SIDDEKLKEEFAPYGTITSARVMRDQEGNSKGFGFVCFSSPEEATKAMT

EKNQQIVAGKPLYVAIAQRKDVRRSQLAQQIQARNQIRFQQQQQQQAAA

AAAGMPGQYMPQMFYGVMAPRGFPGPNPGMNGPMGAGIPKNGMVPPPQQ

FAGRPNGPMYQGMPPQNQFPRHQQQHYIQQQKQRQALGEQLYKKVSAKI

DDENAAGKITGMILDLPPQQVIQLLDNDEQFEQQFQEALAAYENFKKEQ

EAQAGGGGSGGGGSTQDEVQGPHAGKSTVGGGGSGEPTSDQQPAVEAPV

VQEETTSSPQKNSGYVKNTAGSGAPRNGKYDGNRKNSRPYNQRGNNNNN

NGSSSNKHYQKYNQPAYGVSAGYIPNYGVSAEYNPLYYNQYQQQQQLYA

AAYQTPMSGQGYVPPVVSPAAVSAKPAKVEITNKSGEHIDIASIAHPHT

HSHSQSHSRAVPVVSPPANVTVAAAVSSSVSPSASPAVKVQSPAANGKE

QSPAKPEEPKKDTLIVNDFLEQVKRRKAALAAKKAVEEKGPEEPKESVV

GTDTDASVDTKTGPTATESAKSEEAQSESQEKTKEEAPAEPKPLTLAEK

LRLKRMEAAKQASAKTEELKTEESKPEETKTEELKTEESKPEETKTEEL

KTEETKSEELKTEEPKAEESKAEEPKPEEPKTEEPTTEQPKSDEPKSEE

SKTEEPKTEVLKTEEPKSEESKPAEPKTEETATEETATEANAEEGEPAP

AGPVETPADVETKPREEAEVEDDGKITMTDFLQKLKEVSPVDDIYSFQY

PSDITPPNDRYKKTSIKYAYGPDFLYQFKEKVDVKYDPAWMAEMTSKIV
```

-continued

```
IPPKKPGSSGRGEDRFSKGKVGSLRSEGRSGSRSNSKKKSKRDDRKSNR

SYTSRKDRERFREEEVEEPKVEVAPLVPSANRWVPKSKMKKTEVKLAPD

GTELYDAEEASRKMKSLLNKLTLEMFEPISDDIMKIANQSRWEEKGETL

KIVIQQIFNKACDEPHWSSMYAQLCGKVVKDLDDSIKDSETPDKTGSHL

VLHYLVQRCQTEFQTGWTDQLPTNEDGTPLQPEMMSDEYYKMAAAKRRG

LGLVRFIGFLYRSNLLTSRMVFFCFKRLMKDIQNSPTEDTLESVCELLE

TIGEQFEGARIQVTAEAVIEGSSLLDTLFDQIKNVIENGDISSRIKFKL

IDIVELREKRNWNSKNKNDGPKTIAQIHEEEALKRALEERERERDRHGS

RGGSRRMNSERNSSRRDFSSHSHSHNQNRDGFTTTRSSSVRYSEPKKEE

QAPTPTKSSGGAANMFDALMDAEDD.
```

In the present invention, the fusion protein of the present invention can significantly improve the in-vitro protein synthesis ability of a cell-free and in-vitro protein synthesis system (especially a yeast-based in-vitro protein synthesis system).

In-Vitro Protein Synthesis System

The fusion protein of the present invention is used for improving the protein synthesis ability of an in-vitro protein synthesis system.

A typical in-vitro protein synthesis system is a yeast-based in-vitro protein synthesis system.

Yeast has advantages of simple culture, highly efficient protein folding and post-translational modification ability. Wherein, *Saccharomyces cerevisiae* and *Pichia pastoris* are model organisms for expressing complex eukaryotic proteins and membrane proteins. Yeast can also be used as materials for preparing in-vitro translation systems.

*Kluyveromyces* is a kind of ascosporous yeast, among which *Kluyveromyces marxianus* and *Kluyveromyces lactis* are widely used in industry. For example, *Kluyveromyces lactis* is a kind of yeast which can use lactic acid as its sole carbon source and energy source. Compared with other yeasts, *Kluyveromyces lactis* has many advantages, such as superstrong secretion ability, good large-scale fermentation characteristics, food safety level, post-translational modification ability and the like, and also has shown great potential to be used as a host system to express pharmaceutical proteins.

In the present invention, the yeast-based in-vitro protein synthesis system is not particularly limited, and a preferred yeast-based in-vitro protein synthesis system is a *Kluyveromyces* expression system (preferably a *Kluyveromyces lactis* expression system).

In the present invention, *Kluyveromyces* (such as *Kluyveromyces lactis*) is not particularly limited and includes any *Kluyveromyces* (such as *Kluyveromyces lactis*) strain that is capable of increasing the efficiency of protein synthesis.

In a preferred embodiment, the yeast-based in-vitro protein synthesis system of the present invention is an expression system based on a genetically modified *Kluyveromyces lactis* strain.

In a preferred embodiment, the present invention provides an in-vitro cell-free protein synthesis system, including:
   (a) yeast cell extract;
   (b) polyethylene glycol;
   (c) optional exogenous sucrose; and
   (d) an optional solvent, wherein the solvent is water or an aqueous solvent.

In another preferred embodiment, said polyethylene glycol is selected from the group consisting of: PEG3000, PEG8000, PEG6000, PEG3350, and the combination thereof.

In another preferred embodiment, said polyethylene glycol includes polyethylene glycol with a molecular weight (Da in units) of 200-10000, preferably, polyethylene glycol with a molecular weight of 3000-10000.

In another preferred embodiment, in the protein synthesis system, the concentration (v/v) of Component (a) is 20-70%, preferably 30-60%, and more preferably 40-50%, as calculated by the total volume of the protein synthesis system.

In another preferred embodiment, in the protein synthesis system, the concentration (w/v, such as g/ml) of Component (b) is 0.1-8%, preferably 0.5-4%, and more preferably 1-2%.

In another preferred embodiment, in the protein synthesis system, the concentration of Component (c) is 0.03-40 wt %, preferably 0.08-10 wt %, and more preferably 0.1-5 wt %, as calculated by the total weight of the protein synthesis system.

In a particular preferred embodiment, the in-vitro protein synthesis system provided by the present invention consists of: yeast cell extract, 4-hydroxyethyl piperazineethanesulfonic acid, potassium acetate, magnesium acetate, adenosine triphosphate (ATP), guanosine triphosphate (GTP), cytidine triphosphate (CTP), thymine triphosphate (TTP), amino acid mixture, creatine phosphate, dithiothreitol (DTT), creatine phosphate kinase, RNase inhibitor, luciferin, DNA of luciferase and RNA polymerase.

In the present invention, the RNA polymerase is not particularly limited, and can be one kind of RNA polymerase or the combination of more kinds of RNA polymerases; a typical RNA polymerase is T7 RNA polymerase.

In the present invention, the proportion of the yeast cell extract in the in-vitro protein synthesis system is not particularly limited. Generally, the content of the yeast cell extract is 20-70% relative to the in-vitro protein synthesis system, preferably 30-60%, and more preferably 40-50%.

In the present invention, the yeast cell extract does not contain intact cells. A typical yeast cell extract contains factors for protein translation including ribosomes, transfer RNAs and aminoacyl tRNA synthetase, as well as factors required for protein synthesis including initiation factors, elongation factors and release factors mediating termination. In addition, the yeast cell extract also contains some other proteins derived from cytoplasm of the yeast cell, especially soluble proteins.

In the present invention, the protein content of the yeast cell extract is 20-100 mg/mL, preferably 50-100 mg/mL. The method for measuring protein content is Coomassie brilliant blue staining method.

In the present invention, the preparation method of the yeast cell extract is not limited. A preferred preparation method includes the following steps:
(i) providing yeast cells;
(ii) washing the yeast cells to obtain washed yeast cells;
(iii) breaking up the washed yeast cells (or translated as "treat the washed cells with a cell lysis process") to obtain crude yeast extract; and
(iv) treating the crude yeast extract via solid-liquid separation to obtain the liquid phase, that is the yeast cell extract.

In the present invention, the solid-liquid separation method is not limited. A preferred method is centrifugation.

In a preferred embodiment, the centrifugation is carried out in a liquid state.

In the present invention, the centrifugation condition is not particularly limited. A preferred centrifugation condition is 5000-100000 g, preferably 8000-30000 g.

In the present invention, the centrifugation time is not particularly limited. A preferred centrifugation time is 0.5 min-2 h, preferably 20-50 min.

In the present invention, the centrifugation temperature is not particularly limited. Preferably, the centrifugation is carried out at 1-10° C., preferably at 2-6° C.

In the present invention, the washing method is not particularly limited. A preferred washing method is to process at pH 7-8 (preferably pH 7.4) with the use of a washing buffer, wherein the washing buffer is not particularly limited. A typical washing buffer is selected from the group consisting of: potassium 4-hydroxyethyl piperazineethanesulfonate, potassium acetate, magnesium acetate, and the combination thereof.

In the present invention, the method for cell lysis (or translated as "the manner for breaking up cells") is not particularly limited. Preferred cell lysis methods include high-pressure lysis, freeze-thaw (e.g., treatment at liquid-nitrogen low temperature) lysis, etc.

The nucleoside triphosphate mixture in the in-vitro protein synthesis system includes adenosine triphosphate, guanosine triphosphate, cytidine triphosphate, and uridine triphosphate. In the present invention, the concentration of each kind of nucleotide is not particularly limited. The concentration of each kind of nucleotide is usually 0.5-5 mM, preferably 1.0-2.0 mM.

The amino acid mixture in the in-vitro protein synthesis system can include natural or unnatural amino acids, and can include D-type or L-type amino acids. Representative amino acids include, but are not limited to, 20 kinds of natural amino acids: glycine, alanine, valine, leucine, isoleucine, phenylalanine, proline, tryptophan, serine, tyrosine, cysteine, methionine, asparagine, glutamine, threonine, aspartic acid, glutamic acid, lysine, arginine and histidine. The concentration of each kind of amino acid is usually 0.01-0.5 mM, preferably 0.02-0.2 mM, such as 0.05 mM, 0.06 mM, 0.07 mM, 0.08 mM, etc.

In a preferred embodiment, the in-vitro protein synthesis system further contains polyethylene glycol or the like. The concentration of polyethylene glycol or the like is not particularly limited. Usually, the concentration (w/v) of polyethylene glycol or the like is 0.1-8%, preferably 0.5-4%, and more preferably 1-2%, as calculated by the total weight of the protein synthesis system. Representative examples of PEG include, but are not limited to, PEG3000, PEG8000, PEG6000 and PEG3350. It should be understood that the system of the present invention can also include polyethylene glycol with other various molecular weights (e.g., PEG200, 400, 1500, 2000, 4000, 6000, 8000, 10000, etc.).

In a preferred embodiment, the in-vitro protein synthesis system further contains sucrose. The concentration of sucrose is not particularly limited. Usually, the concentration of sucrose is 0.03-40 wt %, preferably 0.08-10 wt %, and more preferably 0.1-5%, as calculated by the total weight of the protein synthesis system.

A particularly preferred in-vitro protein synthesis system further contains, besides the yeast extract, the following components including: 22 mM pH7.4 4-hydroxyethyl piperazineethanesulfonic acid, 30-150 mM potassium acetate, 1.0-5.0 mM magnesium acetate, 1.5-4 mM nucleoside triphosphate mixture, 0.08-0.24 mM amino acid mixture, 25 mM creatine phosphate, 1.7 mM dithiothreitol, 0.27 mg/mL creatine phosphate kinase, 1%-4% polyethylene glycol, 0.5%-2% sucrose, 8-20 ng/μl DNA of firefly luciferase, and 0.027-0.054 mg/mL T7 RNA polymerase.

In a preferred embodiment, the yeast-based in-vitro protein synthesis system of the present invention also contains: (a) the fusion protein according to the present invention, that is, a Pab1-eIF4G fusion protein.

In a preferred embodiment, the yeast-based in-vitro protein synthesis system of the present invention also includes eIF4G protein, wherein the expression of the eIF4G protein of the present invention is induced by a constitutive or inducible promoter (e.g., pScTEF1, pScPGK1, pKlTEF1, pKlPGK1, pScADH1, pScTPI1, pScTDH3, pKlADH1, pKlTPI1, pKlTDH3 or the like) derived from yeast such as *Saccharomyces cerevisiae, Kluyveromyces* or the like.

In the present invention, the in-vitro protein synthesis system containing the fusion protein of the present invention can significantly enhance the in-vitro protein synthesis ability. In addition, the in-vitro protein synthesis system containing the combination of the fusion protein and the eIF4G protein of the present invention has higher in-vitro protein synthesis ability.

A kind of preferred yeast-based in-vitro protein synthesis systems was described in a prior application by the present inventors, CN201710125619.9, which is incorporated entirely herein by reference. The yeast-based in-vitro protein synthesis system in this document does not use the fusion protein described in the present invention.

Typically, the yeast-based in-vitro protein synthesis system of the present invention contains: (a) yeast cell extract; (b) optional polyethylene glycol; (c) optional exogenous sucrose; and (d) an optional solvent, wherein the solvent is water or an aqueous solvent; and (ii) the fusion protein according to the present invention.

In another preferred embodiment, the cell-free protein synthesis system also includes one or more components selected from the group consisting of:
(e1) substrate for RNA synthesis;
(e2) substrate for proteins synthesis;
(e3) magnesium ions;
(e3) potassium ions;
(e5) a buffering agent (or translated as a buffer in the present invention);
(e6) RNA polymerase; and
(e7) an energy regeneration system.

In another preferred embodiment, in the protein synthesis system, the concentration of Component (e1) is 0.1-5 mM, preferably 0.5-3 mM, and more preferably 1-1.5 mM.

In another preferred embodiment, the yeast cell extract is an aqueous extract of yeast cells.

In another preferred embodiment, the yeast cell extract does not contain long-chain nucleic acid molecules endogenously from the yeast.

In another preferred embodiment, the substrate for RNA synthesis includes: nucleoside monophosphate, nucleoside triphosphate, and the combination thereof.

In another preferred embodiment, the substrate for protein synthesis includes: 1-20 kinds of natural amino acids, and unnatural amino acids.

In another preferred embodiment, the magnesium ions derive from a magnesium ion source, and the magnesium ion source is selected from the group consisting of: magnesium acetate, magnesium glutamate and the combination thereof.

In another preferred embodiment, the potassium ions derive from a potassium ion source, and the potassium ion source is selected from the group consisting of: potassium acetate, potassium glutamate and the combination thereof.

In another preferred embodiment, the energy regeneration system is selected from the group consisting of: a creatine phosphate/creatine phosphate kinase system, an energy system through a glycolytic pathway or the glycolytic intermediate metabolites, and the combination thereof.

In another preferred embodiment, the cell-free protein synthesis system also includes (f1) synthetic tRNA.

In another preferred embodiment, the buffering agent is selected from the group consisting of: 4-hydroxyethyl piperazineethanesulfonic acid, tris(hydroxymethyl)aminomethane (or trimethylolaminomethane), and the combination thereof.

In another preferred embodiment, the cell-free protein synthesis system also includes (g1) exogenous DNA molecules for guiding protein synthesis.

In another preferred embodiment, the DNA molecule is linear.

In another preferred embodiment, the DNA molecule is circular.

In another preferred embodiment, the DNA molecule contains a sequence encoding an exogenous protein.

In another preferred embodiment, the sequence encoding an exogenous protein can be a genomic sequence or a cDNA sequence.

In another preferred embodiment, the sequence encoding an exogenous protein also includes a promoter sequence, a 5' untranslated sequence, or/and a 3' untranslated sequence.

Main advantages of the present invention include as follows.
(a) The present invention disclosed, for the first time, the modification of genes in cells which thereby improved the protein synthesis efficiency of the in vitro translation system, with the help of a highly efficient cell transformation platform by using genetic engineering technique.
(b) The present invention disclosed, for the first time, a fusion protein, and the fusion protein of the present invention can significantly enhance the in-vitro protein synthesis ability.
(c) The present invention also disclosed for the first time that the insertion of a constitutive or inducible promoter (e.g., pScTEF1, pScPGK1, pKlTEF1, pKlPGK1, pScADH1, pScTPI1, pScTDH3, pKlADH1, pKlTPI1, pKlTDH3 or the like) in front of the eIF4G element can greatly improve the in-vitro protein synthesis ability.
(d) The present invention disclosed, for the first time, the modification of eIF4G through CRISPR-Cas9 gene editing technology, thereby greatly enhancing the in-vitro protein synthesis ability.
(e) The present invention disclosed for the first time that while the fusion protein of the present invention improved the efficiency of the in-vitro translation system, the expression level of the element eIF4G of the fusion protein of the present invention did not increase.

Example 1

Theoretical Model for Improving Protein Synthesis Via Genetic Modification

In the present invention, the expression of translation initiation factors eIF4G and Pab1 in *K. lactis* is optimized by using CRISPR-Cas9 gene editing technology to improve the efficiency of the in-vitro cell-free translation system.

Example 2

Modification of Translation Initiation Factors By Using CRISPR-Cas9 Technology to Improve the Efficiency of the In-Vitro Translation System 2.1 Insertion of a Strong Promoter in Front of Translation Initiation Factor KleIF4G by Using CRISPR-Cas9 Technology 2.1.1 Retrieval of a KleIF4G Sequence and Determination of a CRISPR gRNA Sequence The eIF4G is an important factor in the process of translation initiation. In the current report, there is no case in which the in-vitro translation activity has been improved by optimizing the expression of endogenous eIF4G by using gene editing technology. In the present invention, the expression of the translation initiation factor KleIF4G was modified by using CRISPR-Cas9 gene editing technology according to the theoretical model in Example 1 to improve the efficiency of the in-vitro cell-free translation system.

i. Based on the eIF4G gene sequence in *S. cerevisiae*, BLAST alignment analysis was carried out in the NCBI database to identify an eIF4G-homologous gene sequence in *Kluyveromyces lactis* which was termed as KleIF4G (which was located at 421863 . . . 424928 of chromosome A). The insertion of a segment of labeled DNA at the tail of this gene was taken as an example herein, and other target genes, insertion sites as well as insertion sequences can be manipulated in a similar way.

ii. The gRNA sequence was identified by searching for the adjacent PAM sequence (NGG) nearby the initiation codon of the KleIF4G gene. The principle for selecting the gRNA is that the GC content should be moderate (the standard in the present invention is that the GC content is 40-60%); and the existence of a poly T structure should be avoided. Finally, the optimized KleIF4G gRNA sequence determined by the present invention was CGGTTTTTCAAAGCAGATAT (SEQ ID NO.: 6) which was located at 424927 . . . 424936 of the chromosome A.

2.1.2 Construction of a Plasmid by Inserting a Strong Promoter in Front of KleIF4G which was Mediated by CRISPR-Cas9

In order to achieve the over-expression of KleIF4G, promoters of pScTEF1, pScPGK1, pKlTEF1 and pKlPGK1 were inserted respectively in front of the KleIF4G gene by using CRISPR-Cas technology in the present invention. The methods for construction and transformation of the plasmid were described below.

i. Construction of CRISPR Plasmid

PCR amplification was carried out by using primer PF1: CGGTTTTTCAAAGCAGATATGTTTAGAGCTAGAAATAGCAAGTTAAAATAAGGCTAGTCCG (SEQ ID NO.: 7), primer PR1: GCTCTAAAACATATCTGCTTTGAAAAACCGAAAGTCCCATTCGCCACCCG (SEQ ID NO.: 8) and a pCAS plasmid as template. 17 μL of the amplification product was mixed, 1 μL of DpnI and 2 μL of 10× digestion buffer were added, and then the mixture was incubated in a bath at 37° C. for 3 h. 10 μL of the DpnI-treated product was added into 100 μL of DH5α competent cells. The mixture was placed on ice for 30 min and heat shocked at 42° C. for 45 s, followed by the addition of 1 mL of LB liquid medium, and then incubated with shaking at 37° C. for 1 h. Thereafter, the mixture was coated onto a Kan-resistant LB solid medium, and then inverted culture was carried out at 37° C. until monoclonal colonies (also translated as monoclones in the present) grew out. Five monoclonal colonies were picked out and then cultured with shaking in an LB liquid medium. After being detected PCR-positive and confirmed by sequencing, the plasmid was extracted and stored, named pKM-CAS1.0-KleIF4G (refer to FIG. 1).

ii. Construction and Amplification of a Donor DNA Plasmid

In order to facilitate the storage and amplification of the linear donor DNA, in the present invention, the donor DNA was inserted into a pMD18 plasmid first, and then amplified via PCR to obtain the linear donor DNA sequence.

PCR amplification was carried out by using a *Kluyveromyces lactis* genomic DNA as template and with primer PF2: GAGCTCGGTACCCGGGGATCCTCTAGAGATAATAAAATTTCAACCTTTAAGCCATTGAATTTTACCATTACG (SEQ ID NO.: 9) and primer PR2: GCCAAGCTTGCATGCCTGCAGGTCGACGATCTTGTTAGTAATCTCAACCTTCGCTGG (SEQ ID NO.: 10); PCR amplification was also carried out by using a pMD18 plasmid as template and with primer pMD18-F: ATCGTCGACCTGCAGGCATG (SEQ ID NO.: 11) and primer pMD18-R: ATCTCTAGAGGATCCCCGGG (SEQ ID NO.: 12). 8.5 μL of each of the two amplification products were mixed, 1 μL of DpnI and 2 μL of 10× digestion buffer were added, and then the mixture was incubated in a bath at 37° C. for 3 h. 10 μL of the DpnI-treated product was added into 100 μL of DH5a competent cells. The mixture was placed on ice for 30 min and heat shocked at 42° C. for 45 s, followed by the addition of 1 mL of LB liquid medium, and then incubated with shaking at 37° C. for 1 h. Thereafter, the mixture was coated onto an Amp-resistant LB solid medium and then inverted culture was carried out at 37° C. until monoclonal colonies grew out. Five monoclonal colonies were picked out and then cultured with shaking in an LB liquid medium. After being detected PCR-positive and confirmed by sequencing, the plasmid was extracted and stored, named pKM-KleIF4G-DD.

PCR amplification was carried out by using the pKM-KleIF4G-DD plasmid as template, with primer PF3: ATGGGCGAACCTACATCCGATC (SEQ ID NO.: 13) and primer PR3: ATCTGCTTTGAAAAACCGCTCTTTCTCTC (SEQ ID NO.: 14); PCR amplification (pScTEF1 promoter mediated amplification) was carried out by using an *S. cerevisiae* genomic DNA as template, and with primer PF4: AGAGAGAAAGAGCGGTTTTTCAAAGCAGATCCACACACCATAGCTTCAAAAT GTTTCTAC (SEQ ID NO.: 15) and primer PR4: TGGTTGCTGATCGGATGTAGGTTCGCCCATCTTAGATTAGATTGCTATGCTTTC TTTCTAATGAGC (SEQ ID NO.: 16); PCR amplification (pScPGK1 promoter mediated amplification) was carried out by using an *S. cerevisiae* genomic DNA as template, and with primer PF5: AGAGAGAAAGAGCGGTTTTTCAAAGCAGATAGACGCGAATTTTTCGAAGAA GTACC (SEQ ID NO.: 17) and primer PF5: AGCTTCAACAGCTGGTTGCTGATCGGATGTAGGTTCGCCCATTGTTTTATATTT GTTGTAAAAAGTAGATAATTACTTCCTTGATGATC (SEQ ID NO.: 18); PCR amplification (pKlTEF1 promoter mediated amplification) was carried out by using a *Kluyveromyces lactis* genomic DNA as template, and with primer PF6: AGAGAGAAAGAGCGGTTTTTCAAAGCAGATGAGCCTGTCCAAGCAAATGCC (SEQ ID NO.: 19) and primer PR6: TGGTTGCTGATCGGATGTAGGTTCGCCCATTTTTAATGTTACTTCTCTTGCAGT TAGGGAAC (SEQ ID NO.: 20);

PCR amplification (pKlPGK1 promoter mediated amplification) was carried out by using a *Kluyveromyces lactis* genomic DNA as template, and with primer PF7: AGAGAGAAAGAGCGGTTTTTCAAAGCA-GATGTTCCTCATCACTAGAAGCCGA ACTG (SEQ ID NO.: 21) and primer PR7: AGCTT-CAACAGCTGGTTGCTGATCGGATGTAGGTTCGCC-CATTTTTATTAATTC TTGATCGATTTTTTTGTTAT-TTCTGAAGTAACTCT (SEQ ID NO.: 22). The PF3/PR3 amplification product was mixed with PF4/PR4 amplification product, PF5/PR5 amplification product, PF6/PR6 amplification product and PF7/PR7 amplification product, respectively, to construct pKM-pScTEF1-KleIF4G-DD, pKM-pScPGK1-KleIF4G-DD, pKM-pKlTEF1-KleIF4G-DD and pKM-pKlPGK1-KleIF4G-DD, respectively (according to FIGS. 2, 3, 4 and 5). The specific steps include as follows: 8.5 μL of each of the two PCR amplification products were mixed, 1 μL of DpnI and 2 μL of 10× digestion buffer were added, and then the mixture was incubated in a bath at 37° C. for 3 h. 10 μL of the DpnI-treated product was added into 100 μL of DH5α competent cells. The mixture was placed on ice for 30 min and heat shocked at 42° C. for 45 s, followed by the addition of 1 mL of LB liquid medium, and then incubated with shaking at 37° C. for 1 h. Thereafter, the culture solution was coated onto an Amp-resistant LB solid medium, and then inverted culture was carried out at 37° C. until single clone colonies grew out. Five monoclonal colonies were picked out and then cultured with shaking in an LB liquid medium. After being detected PCR-positive and confirmed by sequencing, the plasmid was extracted and stored.

2.1.3 Transformation of *Kluyveromyces lactis* and Positive Identification i. A *Kluyveromyces lactis* yeast solution was streaked and cultured on YPD solid medium. A single clone was picked out and cultured with shaking in 25 mL 2×YPD liquid medium overnight. 2 mL of the yeast solution was taken and continued to be cultured with shaking in 50 mL 2×YPD liquid medium for 2-8 h. Yeast cells were collected by centrifugation at 3000 g for 5 min at 20° C., resuspended with the addition of 500 μL of sterile water. Cells were collected by centrifugation under the same condition. A competent cell solution (5% v/v glycerol and 10% v/v DMSO) was prepared and the yeast cells were dissolved in 500 μL of this solution. 50 μL aliquots were aliquoted into 1.5 mL centrifuge tubes and saved at −80° C.

Competent cells were thawed at 37° C. for 15-30 s, centrifuged at 13000 g for 2 min, and the supernatant was removed. Transformation buffer was prepared as follows: 260 μL of PEG3350 (50% (w/v)), 36 μL of LiAc (1.0 M), 20 μL of carrier DNA (5.0 mg/mL), 15 μL of Cas9/gRNA plasmid and 10 μL of donor DNA, with sterile water added until to a final volume of 360 μL. After heat shock, centrifugation was carried out at 13000 g for 30 s to remove the supernatant. 1 mL of YPD liquid medium was added and the mixture was incubated for 2-3 h. 200 μL of the mixture was pipetted and coated onto an YPD (200 μg/mL G418) solid medium and then incubated for 2-3 days until monoclonal colonies appeared.

ii. 10-20 monoclonal colonies were picked out from the plate with transformed *Kluyveromyces lactis* cells, and cultured with shaking in 1 mL YPD (200 μg/mL G418) liquid medium overnight. Corresponding samples were detected by PCR by using the yeast solution as template and with CRISPR Insertion Check primers. Strains that were positive for PCR and identified by sequencing, were determined as positive strains.

2.2 Fusion of KleIF4G with a High-Expressed Gene Via CRISPR-Cas9 Technology 2.2.1 Retrieval of a KlTDH3 Sequence and Determination of a CRISPR gRNA Sequence In *S. cerevisiae*, TDH3 exists in a form of tetramer and is involved in catalytic reactions of the glycolytic pathway. Its promoter pTDH3 is a durable strong promoter widely used in genetic engineering. In order to achieve sufficient expression of KleIF4G in *Kluyveromyces lactis* and to form a locally high concentration when the function of translation initiation is being performed, the KleIF4G gene is linked to the 3' end of the TDH3 gene ORF (open reading frame) of *Kluyveromyces lactis* in the present invention.

i. Based on the TDH3 gene sequence in *S. cerevisiae*. BLAST alignment analysis was carried out in the NCBI database to identify the TDH3-homologous gene sequences in *Kluyveromyces lactis*. After blasting, two TDH3-homologous genes were found in the *Kluyveromyces lactis* genome, which were named KlTDH3-1 (located at 1024297 . . . 1025292 of chromosome A) and KlTDH3-2 (located at 1960417 . . . 1961406 of chromosome F) respectively in the present invention. Inserting a segment of labeled DNA at the tail of this gene was taken as an example herein, and other target genes, insertion sites as well as insertion sequences can be manipulated in a similar way.

ii. PAM sequences (NGG) were searched for nearby the termination codon of the KlTDH3 gene, and KLTDH3 gRNA sequences were identified (KlTDH3-1: CTTGTTGCTAAGAACTAAAG (SEQ ID NO.: 23) located at 1024272 . . . 1024291 of chromosome A, and KlTDH3-2: CTCTGAAAGAGTTGTCGATT (SEQ ID NO.: 24) located at 1960378 . . . 1960397 of chromosome F).

2.2.2 Construction of a Plasmid by Integrating KleIF4G into the KlTDH3 Site, Which was Mediated by CRISPR-Cas9

Figure 6:
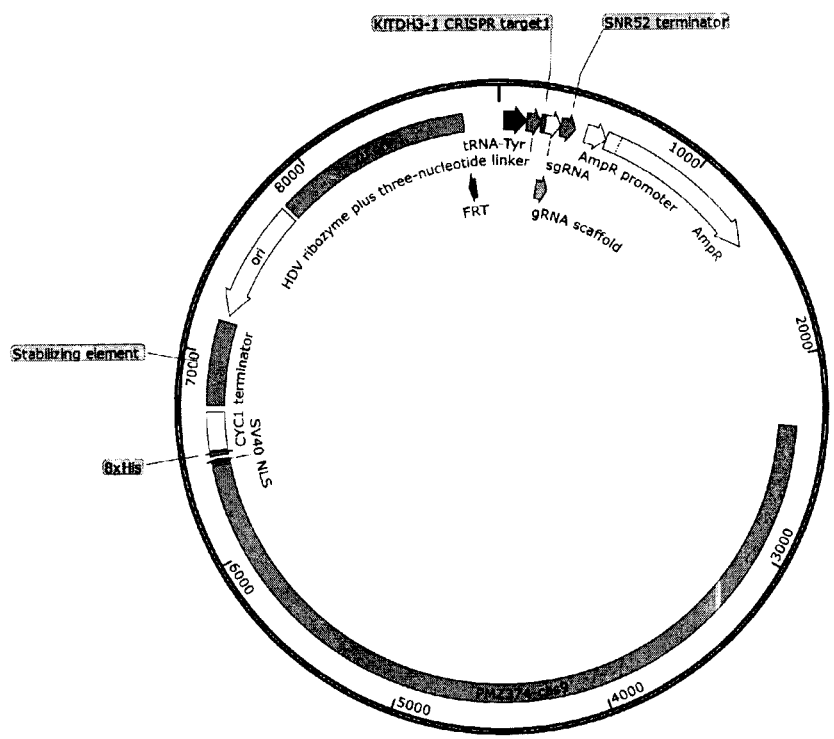
FIG. 6 shows the plasmid map of pKM-CAS1.0-KlTDH3-1.
Figure 7:
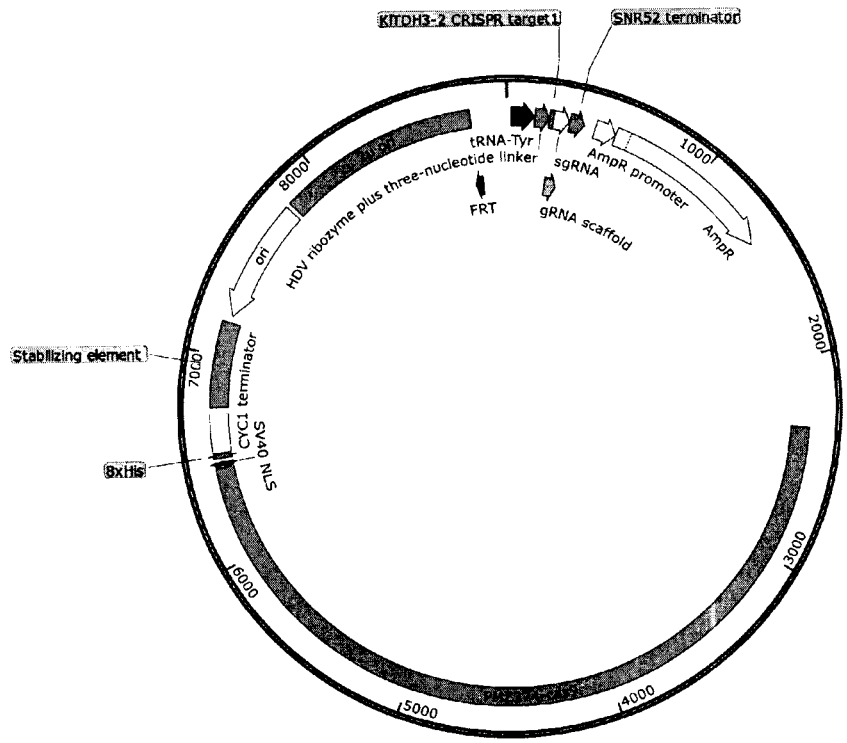
FIG. 7 shows the plasmid map of pKM-CAS1.0-KlTDH3-2.

Construction of CRISPR Plasmid i. For the KlTDH3-1 sequence, PCR amplification was carried out by using a pCAS plasmid as template and with primer PF8: CTTGTTGCTAAGAACTAAAGGTTT-TAGAGCTAGAAATAGCAAGTTAAAAT (SEQ ID NO.: 25) and primer PR8: GCTCTAAAACCTTTAGTTCT-TAGCAACAAGAAAGTCCCATTCGCCACCCG (SEQ ID NO.: 26). 17 μL of the amplification product was mixed, 1 μL of DpnI and 2 of 10× digestion buffer were added, and the mixture was then incubated in a bath at 37° C. for 3 h. 10 μL of the DpnI-treated product was added into 100 μL of DH5a competent cells. The mixture was placed on ice for 30 min, and heat shocked at 42° C. for 45 s, followed by the addition of 1 mL of LB liquid medium, and then incubated with shaking at 37° C. for 1 h. Thereafter, the mixture was coated onto a Kan-resistant LB solid medium, and then inverted culture was carried out at 37° C. until monoclonal colonies grew out. Five monoclonal colonies were picked out and then cultured with shaking in an LB liquid medium. After being detected PCR-positive and being confirmed by sequencing, the plasmid was extracted and stored, named pKM-CAS1.0-KlTDH3-1 (refer to FIG. 6).

ii. For the KlTDH3-2 sequence, PCR amplification was carried out by using a CAS plasmid as template and with primer PF9: CTCTGAAAGAGTTGTCGATTGTTT-TAGAGCTAGAAATAGCAAGTTAAAAT (SEQ ID NO.: 27) and primer PR9: GCTCTAAAACAATCGACAACTCTTTCAGA GAAAGTCCCATTCGCCACCCG (SEQ ID NO.: 28). 17 μL of the amplification product was mixed, 1 μL of DpnI and 2 of 10× digestion buffer were added, and then the mixture was incubated in a bath at 37° C. for 3 h. 10 μL of the DpnI-treated product was added into 100 μL of DH5α competent cells. The mixture was placed on ice for 30 min and heat shocked at 42° C. for 45 s, followed by the addition of 1 mL of LB liquid medium, and then incubated with shaking at 37° C. for 1 h. Thereafter, the mixture was coated onto a Kan-resistant LB solid medium, and then inverted culture was carried out at 37° C. until monoclonal colonies grew out. Five monoclonal colonies were picked out and then cultured with shaking in an LB liquid medium. After being detected PCR-positive and being confirmed by sequencing, the plasmid was extracted and stored, named pKM-CAS1.0-KlTDH3-2 (refer to FIG. 7).

2.2.3 Construction and Amplification of a Donor DNA Plasmid

In order to facilitate the storage and amplification of the linear donor DNA, in the present invention, the donor DNA was inserted into a pMD18 plasmid first, and then amplified via PCR to obtain the linear donor DNA sequence.

i. For the KlTDH3-1, PCR amplification was carried out by sing a *Kluyveromyces lactis* genomic DNA as template and with primer PF10: GAGCTCGGTACCCGGG-GATCCTCTAGAGATCATCCACTCCATCACCGC-TACCC AA (SEQ ID NO.: 29) and primerPR10: GCCAAGCTGCATGCCTGCAGGTCGACGAT-CAACGTCCCCATCTACAAGAGC (SEQ ID NO.: 30); PCR amplification was carried out by using a pMD18 plasmid as template and with primer pMD18-F: ATCGTCGACCTGCAGGCATG (SEQ ID NO.: 31) and primer pMD18-R: ATCTCTAGAGGATCCCCGGG (SEQ ID NO.: 32). 8.5 μL of each of the two amplification products were mixed, 1 μL of DpnI and 2 μL of 10× digestion buffer were added, and then the mixture was incubated in a bath at 37° C. for 3 h. 10 μL of the DpnI-treated product was added into 100 μL of DH5α competent cells. The mixture was placed on ice for 30 min and heat shocked at 42° C. for 45 s, followed by the addition of 1 mL of LB liquid medium, and then incubated with shaking at 37° C. for 1 h. Thereafter, the mixture was coated onto an Amp-resistant LB solid medium, and then inverted culture was carried out at 37° C. until monoclonal colonies grew out. Five monoclonal colonies were picked out and then cultured with shaking in an LB liquid medium. After being detected PCR-positive and being confirmed by sequencing, the plasmid was extracted and stored, named pKM-KlTDH3-1-DD.

Figure 8:
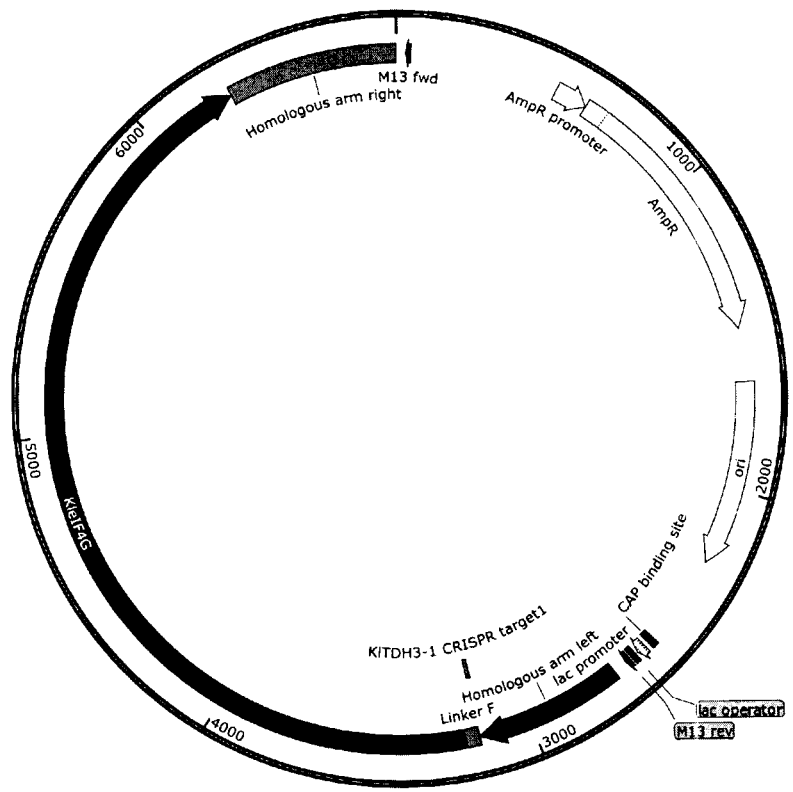
FIG. 8 shows the plasmid map of pKM-KlTDH3-1-F-KleIF4G-DD.

Amplification was carried out by using pKM-KlTDH3-1-DD as template and with primers PF11: GATGCATT-GATGGATGCCGAAGATGATTAAAGAGGTT-GATGTAATTGATATTTT CCTGATAAAATTACTATTG (SEQ ID NO.: 33) and PR11: AGCTGGTTGCTGATCG-GATGTAGGTTCGCCAGATCCACCTCCTTC-CACGTTTG TTGGTCTTGATCCACCTCCACCGTTCT-TAGCAACAAGTTCGACCAAATCG (SEQ ID NO.: 34); amplification was carried out by using a *K. lactis* genomic DNA as template and with primers PF12: GGCGAACCTA-CATCCGATCAGC (SEQ ID NO.: 35) and PR12: TTAAT-CATCTTCGGCATCCATCAATGC (SEQ ID NO.: 36). 8.5 μL of each of the two amplification products, 1 μL of DpnI and 2 μL of 10× digestion buffer were mixed, and then the mixture was incubated in a bath at 37° C. for 3 h. 10 μL of the DpnI-treated product was added into 100 μL of DH5α competent cells. The mixture was placed on ice for 30 min and heat shocked at 42° C. for 45 s, followed by the addition of 1 mL of LB liquid medium, and then incubated with shaking at 37° C. for 1 h. Thereafter, the mixture was coated onto an Amp-resistant LB solid medium, and then inverted culture was carried out at 37° C. until monoclonal colonies grew out. Five monoclonal colonies were picked out and then cultured with shaking in an LB liquid medium. After being detected PCR-positive and being confirmed by sequencing, the plasmids was extracted and stored, named pKM-KlTDH3-1-F-KleIF4G-DD (refer to FIG. 8).

Amplification was carried out by using the pKM-KlTDH3-1-F-KleIF4G-DD plasmid as template and with primers M13-F: GTAAAACGACGGCCAGT (SEQ ID NO.: 37) and M13-R: CAGGAAACAGCTATGAC (SEQ ID NO.: 38) to obtain the linear donor DNA.

ii. For the KlTDH3-2 sequence, PCR amplification was carried out by using a *Kluyveromyces lactis* genomic DNA as template and with primers PF13: GAGCTCGGTACCCGGGGATCCTCTAGAGAT-GAAGCTTTGATGACTACCGTTC (SEQ ID NO.: 39) and PR13: GCCAAGCTTGCATGCCTGCAGGTCGAC-GATGTCTATTGTATCGGAAGAACTGT CA (SEQ ID NO.: 40); PCR amplification was carried out by using a pMD18 plasmid as template and with primers pMD18-F: ATCGTCGACCTGCAGGCATG (SEQ ID NO.: 41) and pMD18-R: ATCTCTAGAGGATCCCCGGG (SEQ ID NO.: 42). 8.5 μL of each of the two amplification products were mixed, 1 μL of DpnI and 2 μL of 10× digestion buffer were added, and then the mixture was incubated in a bath at 37° C. for 3 h. 10 μL of the DpnI-treated product was added into 100 μL of DH5α competent cells. The mixture was placed on ice for 30 min and heat shocked at 42° C. for 45 s, followed by the addition of 1 mL of LB liquid medium, and then incubated with shaking at 37° C. for 1 h. Thereafter, the culture solution was coated onto an Amp-resistant LB solid medium, and then inverted culture was carried out at 37° C. until monoclonal colonies grew out. Five monoclonal colonies were picked out and then incubated with shaking in an LB liquid medium. After being detected PCR-positive and being confirmed by sequencing, the plasmid was extracted and stored, named pKM-KlTDH3-2-DD.

Figure 9:
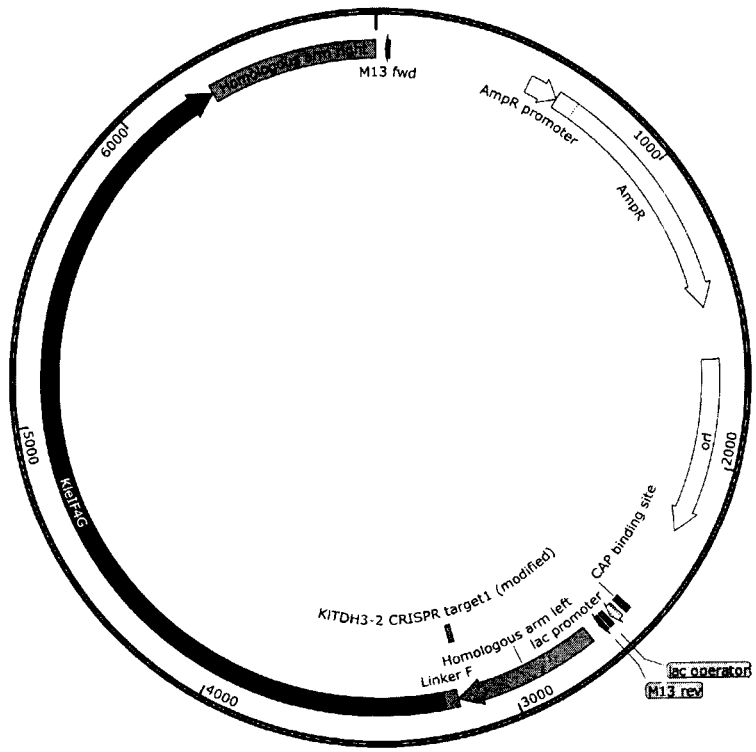
FIG. 9 shows the plasmid map of pKM-KlTDH3-2-F-KleIF4G-DD.

Amplification was carried out by using the pKM-KlTDH3-2-DD as template and with primers PF14: GATG-CATTGATGGATGCCGAAGATGATTAAATTACTCTTT-TAAGTTAACGAACG CTTTTGATGAG (SEQ ID NO.: 43) and PR14: AGCTGGTTGCTGATCG-GATGTAGGTTCGCCAGATCCACCTCCTTC-CACGTTTG TTGGTCTTGATCCACCTC-CACCAGCAACGTGCTCAACtAAgTCaACgACcCTTT CAGAGTAACCGTATTCGTTATCG (SEQ ID NO.: 44); amplification was carried out by using a *Kluyveromyces lactis* DNA as template and with primers PF15: GGCGAACCTACATCCGATCAGC (SEQ ID NO.: 45) and PR15: TTAATCATCTTCGGCATCCATCAATGC (SEQ ID NO.: 46). 8.5 μL of each of the two amplification products, 1 μL of DpnI and 2 μL of 10× digestion buffer were mixed, and then the mixture was incubated in a bath at 37° C. for 3 h. 10 μL of the DpnI-treated product was added into 100 μL of DH5α competent cells. The mixture was placed on ice for 30 min and heat shocked at 42° C. for 45 s, followed by the addition of 1 mL of LB liquid medium, and then incubated with shaking at 37° C. for 1 h. Thereafter, the culture solution was coated onto an Amp-resistant LB solid medium, and then inverted culture was carried out at 37° C. until monoclonal colonies grew out. Five monoclonal colonies were picked out and then cultured with shaking in an LB liquid medium. After being detected PCR-positive and being confirmed by sequencing, the plasmid was extracted and stored, named pKM-KlTDH3-2-F-KleIF4G-DD (refer to FIG. 9).

Amplification was carried out by using the pKM-KlTDH3-2-F-KleIF4G-DD plasmid as template, and with primers M13-F: GTAAAACGACGGCCAGT (SEQ ID NO.: 47) and M13-R: CAGGAAACAGCTATGAC (SEQ ID NO.: 48) to obtain the linear donor DNA.

2.2.4 Transformation of *Kluyveromyces lactis* and Positive Identification i. A *Kluyveromyces lactis* yeast solution was streaked and cultured on YPD solid medium. A single clone was picked out and cultured with shaking in 25 mL 2× YPD liquid medium overnight. 2 mL of the yeast solution was taken and continued to be cultured with shaking in 50 mL 2×YPD liquid medium for 2-8 h. Yeast cells were collected by centrifugation at 3000 g for 5 min under the condition of 20° C., resuspended with the addition of 500 μL of sterile water. Cells were collected by centrifugation under the same condition. A competent cell solution (5% v/v glycerol and 10% v/v DMSO) was prepared and the yeast cells were dissolved in 500 μL of this solution. 50 μL aliquots were aliquoted into 1.5 mL centrifuge tubes and saved at −80° C.

Competent cells were thawed at 37° C. for 15-30 s, centrifuged at 13000 g for 2 min, and the supernatant was removed. Transformation buffer was prepared as follows: 260 μL of PEG3350 (50% (w/v)), 36 μL of LiAc (1.0 M), 20 μL of carrier DNA (5.0 mg/mL), 15 μL of Cas9/gRNA plasmid and 10 μL of donor DNA, with sterile water added until the final volume was 360 μL. After heat shock, centrifugation was carried out at 13000 g for 30 s to remove the supernatant. 1 mL of YPD liquid medium was added and the mixture was incubated for 2-3 h. 200 μL of the culture solution was pipetted and coated onto an YPD (200 μg/mL G418) solid medium and then incubated for 2-3 days until monoclonal colonies appeared.

ii. 10-20 monoclonal colonies were picked out from the culture plate with transformed *Kluyveromyces lactis* cells, and cultured with shaking in 1 mL YPD (200 μg/mL G418) liquid medium overnight. PCR amplification was carried out by using the yeast solution as template, and by using CRISPR Insertion Check primer KlTDH3-1-CICF1 (the inner primer for the KlTDH3-1 sequence): CTTCTACTGCTCCAATGTTCGTCGTT (SEQ ID NO.: 49) and primer KlTDH3-2-CICF1 (the inner primer for the KlTDH3-2 sequence): TTAACGAAGACAAGTACAACGGTGA (SEQ ID NO.: 50), which are paired with primer KleIF4G-CICR2 (the inner primer for the KleIF4G sequence): TTCTCTTCGACAGCCTTCTTAGCAG (SEQ ID NO.:51), respectively. The insertion of KleIF4G at KlTDH3-1 and KlTDH3-2 sites was characterized. Strains with positive PCR results and identified by sequencing were determined as positive strains.

2.3 Fusion of KleIF4G with its Interacting Protein via CRISPR-Cas9 Technology 2.3.1 Retrieval of the KlPab1 Sequence and Determination of the CRISPR gRNA Sequence As mentioned above, the Pab1 protein and the eIF4G protein interact with each other in the translation initiation process. In the present invention, KlPab1 and KleIF4G were fused by using CRISPR-Cas9 gene editing technology to promote the interaction between them and thus to improve the in-vitro translation efficiency.

Based on the Pab1 sequence, a KlPab1 gene sequence (located at 1553322 . . . 1555100 of chromosome C) in *Kluyveromyces lactis* was obtained. PAM sequences (NGG) were searched for nearby the termination codon of the KlPab1 gene, and a gRNA sequence was identified. The principle for selecting a gRNA sequence is that the GC content should be moderate (the standard in the present invention is that the GC content is 40-60%); and the existence of a poly(T) structure should be avoided. Finally, the KlPab1 gRNA sequence determined by the present invention was TGCTTACGAAAACTTCAAGA (SEQ ID NO.: 52) which was located at 1555058 . . . 1555077 of the chromosome C.

Figure 10:
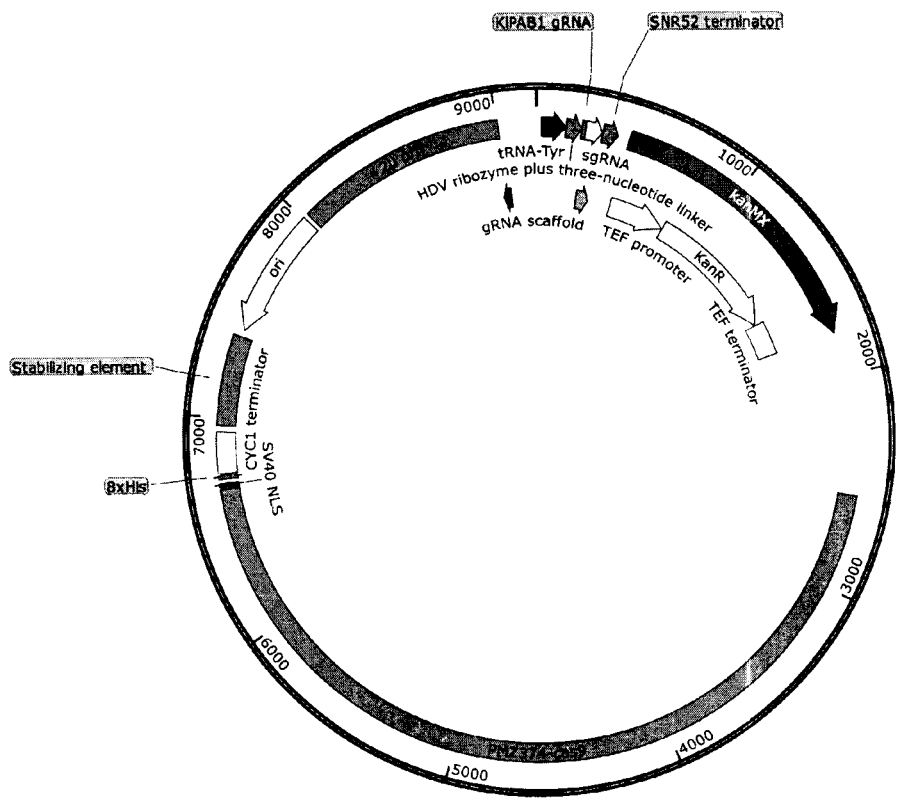
FIG. 10 shows the plasmid map of pKM-CAS1.0-KlPab1.

2.3.2 Construction of a Plasmid with KleIF4G Integrated at KlPab1 Site Via CRISPR-Cas9 Technology i. Construction of a CRISPR Plasmid PCR amplification was carried out by using a pCAS plasmid as template and with primers PF16: TGCTTACGAAAACTTCAAGAGTTTTAGAGCTAGAAATAGCAAGTTAAAATAAGGCTAGTCCG (SEQ ID NO.: 53) and PR16: GCTCTAAAACTCTTGAAGTTTTCGTAAGCAAAAGTCCCATTCGCCACCCG (SEQ ID NO.: 54). 17 μL, of the amplification product was mixed, 1 μL of DpnI and 2 μL, of 10× digestion buffer were added, and then the mixture was incubated in a bath at 37° C. for 3 h. 10 μL, of the DpnI-treated product was added into 100 μL of DH5α competent cells. The mixture was placed on ice for 30 min and heat shocked at 42° C. for 45 s, followed by the addition of 1 mL of LB liquid medium, and then incubated with shaking for at 37° C. 1 h. Thereafter, the mixture was coated onto a Kan-resistant LB solid medium, and then inverted culture was carried out at 37° C. until monoclonal colonies grew out. Five monoclonal colonies were picked out and then cultured with shaking in an LB liquid medium. After being detected PCR-positive and confirmed by sequencing, the plasmid was extracted and stored, named pKM-CAS1.0-KlPab1 (refer to FIG. 10).

ii. Construction and Amplification of a KlPab1-KleIF4G Donor DNA Plasmid

In order to facilitate the storage and amplification of the linear donor DNA, the donor DNA was inserted into a pMD18 plasmid first, and then amplified via PCR to obtain the linear donor DNA sequence.

PCR amplification was carried out by using a *Kluyveromyces lactis* genomic DNA as template and with primers PF17: GAGCTCGGTACCCGGGGATCCTCTAGAGATCCGGTAAGCCATTGTACGTTGCC AT (SEQ ID NO.: 55) and PR17: GCCAAGCTTGCATGCCTGCAGGTCGACGATCAGTATACCGTCCATGTTGATGA CT (SEQ ID NO.: 56); PCR amplification was carried out by using a pMD18 plasmid as template and with primers pMD18-F: ATCGTCGACCTGCAGGCATG (SEQ ID NO.: 57) and pMD18-R: ATCTCTAGAGGATCCCCGGG (SEQ ID NO.: 58). 8.5 μL of each of the two amplification products were mixed, 1 μL of DpnI and 2 μL of 10× digestion buffer were added, and then the mixture was incubated in a bath at 37° C. for 3 h. 10 μL of the DpnI-treated product was added into 100 μL of DH5α competent cells. The mixture was placed on ice for 30 min and heat shocked at 42° C. for 45 s, followed by the addition of 1 mL of LB liquid medium, and then incubated with shaking at 37° C. for 1 h. Thereafter, the mixture was coated onto an Amp-resistant LB solid medium, and then inverted culture was carried out at 37° C. until monoclonal colonies grew out. Five monoclonal colonies were picked out and then cultured with shaking in an LB liquid medium. After being detected PCR-positive and confirmed by sequencing, the plasmid was extracted and stored, named pKM-KlPab1-DD.

Figure 11:
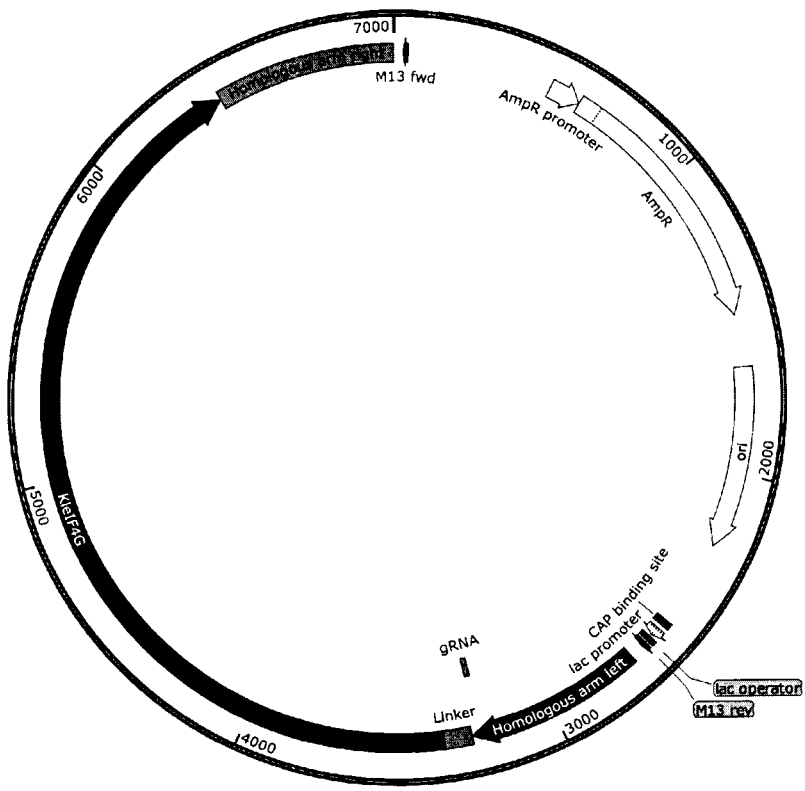
FIG. 11 shows the plasmid map of pKM-KlPab1-KleIF4G-DD.

Amplification was carried out by using the pKM-KlPab1-DD as template and with primer PF18: GATGCATTGATGGATGCCGAAGATGATTAAACTTGATTTTTTGACCTTGATCTT CATCTTGTC (SEQ ID NO.: 59) and primer PR18: CTTGAACTTCATCTTGAGTTGAACCTCCACCTCCAGATCCACCTCCACCAGCT TGAGCTTCTTGTTCtTTtTTaAAaT-TcTCGTAAGCAGCTAAGGCTTC (SEQ ID NO.: 60); amplification was carried out by using a *Kluyveromyces lactis* DNA as template and with primer PF19: GTG-GAGGTTCAACTCAAGATGAAGTTCAAGGTCCA-CATGCTGGTAAGTCTAC TGTTGGTGGAGGTG-GATCTGGCGAACCTACATCCGATCAGC (SEQ ID NO.: 61) and primer PR19: TTAATCATCTTCGGCATCCAT-CAATGC (SEQ ID NO.: 62). 8.5 of each of the two amplification products, 1 μL of DpnI and 2 μL of 10× digestion buffer were mixed, and then the mixture was incubated in a bath at 37° C. for 3 h. 10 of the DpnI-treated product was added into 100 μL of DH5α competent cells. The mixture was placed on ice for 30 min, treated by heat shock at 42° C. for 45 s, followed by the addition of LB liquid medium 1 mL, and then incubated with shaking at 37° C. for 1 h. Thereafter, the mixture was coated onto an Amp-resistant LB solid medium, and then inverted culture was carried out at 37° C. until monoclonal colonies grew out. Five monoclonal colonies were picked out and then cultured with shaking in an LB liquid medium. After being detected PCR-positive and being confirmed by sequencing, the plasmid was extracted and stored, named pKM-KlPab1-KleIF4G-DD (refer to FIG. 11).

Amplification was carried out by using the pKM-KlPab1-KleIF4G-DD plasmid as template and with primers M13-F: GTAAAACGACGGCCAGT (SEQ ID NO.: 63) and M13-R: CAGGAAACAGCTATGAC (SEQ ID NO.: 64) to obtain the linear donor DNA.

2.3.3 Transformation of *Kluyveromyces lactis* and Positive Identification i. A *Kluyveromyces lactis* yeast solution was streaked and cultured on YPD solid medium. A single clone was picked out and cultured with shaking in 25 mL 2× YPD liquid medium overnight. 2 mL of the yeast solution was taken and continued to be cultured with shaking in 50 mL 2×YPD liquid medium for 2-8 h. Yeast cells were collected by centrifugation at 3000 g for 5 min under the condition of 20° C., resuspended with the addition of 500 μL of sterile water. Cells were collected by centrifugation under the same condition. A competent cell solution (5% v/v glycerol and 10% v/v DMSO) was prepared and the yeast cells were dissolved in 500 μL of this solution. 50 μL aliquots were aliquoted into 1.5 mL centrifuge tubes and saved at −80° C.

Competent cells were thawed at 37° C. for 15-30 s, centrifuged at 13000 g for 2 min, and the supernatant was removed. Transformation buffer was prepared as follows: 260 μL of PEG3350 (50% (w/v)), 36 μL of LiAc (1.0 M), 20 μL of carrier DNA (5.0 mg/mL), 15 μL of Cas9/gRNA plasmid and 10 μL of donor DNA, with sterile water added to a final volume 360 μL. After heat shock, centrifugation was carried out at 13000 g for 30 s to remove the supernatant. 1 mL of YPD liquid medium was added and the mixture was incubated for 2-3 h. 200 μL of the culture solution was pipetted and coated onto an YPD (200 μg/mL G418) solid medium and then incubated for 2-3 days until monoclonal colonies appeared.

ii. 10-20 monoclonal colonies were picked out from the plate with transformed *Kluyveromyces lactis* cells, and cultured with shaking in 1 mL YPD (200 μg/mL G418) liquid medium overnight. PCR amplification was carried out by using the yeast solution as template and with primers: KlPAB1-CICF1 (the inner primer for the KlPAB1 sequence): TCTCCAGAAGAAGCTACCAAGGCTA (SEQ ID NO.: 65) and KleIF4G-CICR2 (the inner primer for the KleIF4G sequence): TTCTCTTCGACAGCCTTCT-TAGCAG (SEQ ID NO.: 66). The insertion of KleIF4G at the KlPAB1 site was detected. Strains with positive PCR results and identified by sequencing were determined as positive strains.

Example 3

Determination of the In-Vitro Translation Activity of the Modified Strains

The genetically modified *Kluyveromyces lactis* strains were prepared into in-vitro protein synthesis systems, and firefly luciferase (Fluc) gene as DNA template was added to detect the ability of protein translation of the modified strains. The above-said reaction systems were placed at room temperature 25-30° C., let stand and incubated for about 2-6 h. After the reaction was completed, equal volumes of substrate for Fluc (luciferin) were added into the 96-well white plates or 384-well white plates. The plate was immediately placed in an Envision 2120 multi-mode microplate reader (Perkin Elmer). Read values to obtain the Fluc activity, wherein, the unit for activity is relative light unit (RLU).

Figure 12:
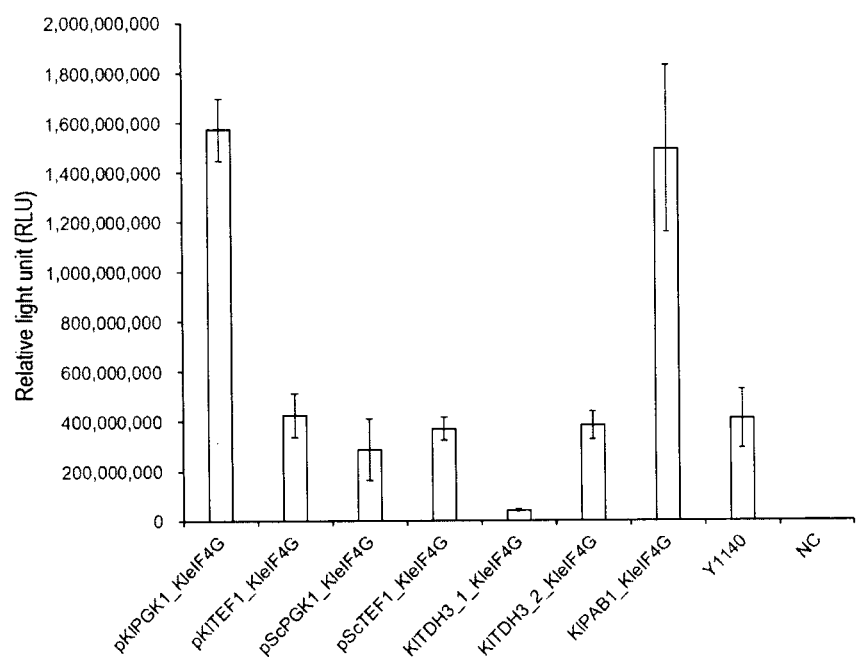
FIG. 12 shows the testing results of the in-vitro translation activity based on genetic modified strains, wherein, the fluorescence intensity of the fluorescent protein is used to indicate the protein expression ability of the in-vitro translation system.

Among the modified structures, both the pKlPGK1::KleIF4G structure formed by inserting the pKlPGK1 promoter in front of KleIF4G and the KlPab1-KleIF4G structure formed by fusing KleIF4G to the C-terminus of KlPab1, showed stronger protein synthesis ability in vitro than that based on the wild-type yeast strain Y1140. The values of relative light units released by corresponding encoded Fluc protein reached $1.57 \times 10^9$ and $1.50 \times 10^9$, respectively, while the value of relative light units of the Fluc protein synthesized in vitro based on the wild-type yeast strain Y1140 was only $4.11 \times 10^8$. It indicates that the modification of KleIF4G can effectively enhance the protein synthesis efficiency of the yeast-based in vitro protein synthesis system (refer to FIG. 12).

Specific effects are shown in Table 2.

TABLE 2

| NO. | Data1 | Data2 | Data3 | Activity | Dilution ratio | Final activity (RLU) |
| --- | --- | --- | --- | --- | --- | --- |
| pKlPGK1_KleIF4G | 33216610 | 28584890 | 32598650 | 31466717 | 50 | $1.57 \times 10^9$ |
| pKlTEF1_KleIF4G | 6685609 | 10189150 | 8594529 | 8489763 | 50 | $4.24 \times 10^8$ |
| pScPGK1_KleIF4G | 4130719 | 8605461 | 4555399 | 5763860 | 50 | $2.88 \times 10^8$ |
| pScTEF1_KleIF4G | 8230202 | 6415045 | 7578242 | 7407830 | 50 | $3.70 \times 10^8$ |
| KlTDH3_1_KleIF4G | 788821 | 751243 | 941381 | 827148.3 | 50 | $4.13 \times 10^7$ |
| KlTDH3_2_KleIF4G | 8676941 | 6496592 | 7904461 | 7692665 | 50 | $3.85 \times 10^8$ |
| KlPAB1_KleIF4G | 22155330 | 33507550 | 34075530 | 29912803 | 50 | $1.50 \times 10^9$ |
| Y1140 | 10925600 | 6729764 | 6997436 | 8217600 | 50 | $4.11 \times 10^8$ |
| NC | | 707 | 965 | | | |

NC represents negative control.

The above experimental results show that the fusion protein of the present invention can significantly enhance the protein synthesis efficiency of the yeast-based in-vitro protein synthesis system through the related modification of the KleIF4G gene of *Kluyveromyces lactis*.

All documents mentioned in the present invention are incorporated by reference in this application, as if each document is individually incorporated by reference. In addition, it should be understood that those skilled in the art, after reading the above-mentioned description, can make various changes or modifications to the present invention, and these equivalent forms also fall within the scope defined by the claims attached to the Application.

What is claimed is:

1. A fusion protein having a structure represented by the general Formula Ia or Formula Ib:

A-B-C  (Ia)

C-B-A  (Ib);

wherein,
A is a Pab1 protein;
B is a linker peptide or not present;
C is a eIF4G protein; and
each "-" is a peptide bond,
wherein the Pab1 protein and the eIF4G protein are both from *Kluyveromyces lactis*, or are both from *Kluyveromyces marxianus*, or are both from *Kluyveromyces dobzhanskii*, and
the Pab1 protein is a polyadenylate binding protein and has a sequence identity greater or equal to 95%, 97%, 98%, or 99% to the protein of SEQ ID NO: 1; and
the eIF4G protein is a translation initiation factor and has a sequence identity greater or equal to 97%, 98%, or 99% to the protein of SEQ ID NO: 2.

2. The fusion protein according to claim 1, wherein the Pab1 protein and the eIF4G protein are both from *Kluyveromyces lactis*, and
the Pab1 protein is a polyadenylate binding protein and has a sequence identity greater or equal to 99% to the protein of SEQ ID NO: 1; and
the eIF4G protein is a translation initiation factor and has a sequence identity greater or equal to 99% to the protein of SEQ ID NO: 2.

3. The fusion protein according to claim 1, wherein the Pab1 protein has the sequence of SEQ ID NO: 1; and the eIF4G protein has the sequence of SEQ ID NO: 2.

4. An isolated polynucleotide, wherein the polynucleotide encodes the fusion protein according to claim 1.

5. A vector, wherein the vector contains the polynucleotide according to claim 4.

6. A host cell, wherein the host cell contains the vector according to claim 5, or wherein the host cell has been modified to integrate the polynucleotide of claim 4 in its genome.

7. An in-vitro protein synthesis system for expressing an exogenous protein, comprising:
(i) a yeast-based in-vitro protein synthesis system which includes (a) yeast cell extract; (b) optional polyethylene glycol; (c) optional exogenous sucrose; and (d) optional solvent, wherein the solvent is water or an aqueous solvent; and
(ii) the fusion protein according to claim 1,
wherein the yeast cell extract is from a same yeast species as the Pab1 protein and the eIF4G protein.

8. The in-vitro protein synthesis system according to claim 7, wherein the in-vitro protein synthesis system further comprises additionally added eIF4G protein, wherein the eIF4G protein is a translation initiation factor and has a sequence identity greater or equal to 97%, 98%, or 99% to the protein of SEQ ID NO: 2.

9. A method for producing the fusion protein according to claim 1, comprising:
(i) culturing the host cell of claim 6 to express the fusion protein of claim 1 under a condition suitable for expression; and
(ii) isolating the fusion protein.

10. A method for expressing an exogenous protein, comprising:
(i) providing a yeast-based in-vitro protein synthesis system which contains the fusion protein of claim 1; and
(ii) incubating the yeast-based in-vitro protein synthesis system in the presence of a nucleic acid encoding an exogenous protein to express the exogenous protein under a condition suitable for protein expression.

11. The fusion protein of claim 1, wherein the fusion protein further comprises a signal peptide, and has the formula of S-A-B-C or S-C-B-A, wherein
A is a Pab1 protein;
B is a linker peptide or not present;
C is an eIF4G protein;
S is a signal peptide; and
each "-" is a peptide bond,
wherein the Pab1 protein and the eIF4G protein are both from *Kluyveromyces lactis*, or are both from *Kluyveromyces marxianus*, or are both from *Kluyveromyces dobzhanskii*, and
the Pab1 protein is a polyadenylate binding protein and has a sequence identity greater or equal to 95%, 97%, 98%, or 99% to the protein of SEQ ID NO: 1; and
the eIF4G protein is a translation initiation factor and has a sequence identity greater or equal to 97%, 98%, or 99% to the protein of SEQ ID NO: 2.

12. The fusion protein according to claim 1, wherein the fusion protein has the amino acid sequence of SEQ ID NO: 3.

13. The fusion protein according to claim 11, wherein the Pab1 protein and the eIF4G protein are both from *Kluyveromyces lactis*; and the Pab1 protein is a polyadenylate binding protein and has a sequence identity greater or equal to 99% to the protein of SEQ ID NO: 1; and the eIF4G protein is a translation initiation factor and has a sequence identity greater or equal to 99% to the protein of SEQ ID NO: 2.

14. The fusion protein according to claim 11, wherein the Pab1 protein has the sequence of SEQ ID NO: 1 and the eIF4G protein has the sequence of SEQ ID NO: 2.

\* \* \* \* \*